United States Patent
Buchanan et al.

(10) Patent No.: US 7,982,085 B2
(45) Date of Patent: *Jul. 19, 2011

(54) IN-LINE PROCESS FOR GENERATING COMONOMER

(75) Inventors: John Scott Buchanan, Lambertville, NJ (US); Timothy D. Shaffer, Hackettstown, NJ (US); James R. Lattner, Laporte, TX (US); John F. Walzer, Seabrook, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 1317 days.

This patent is subject to a terminal disclaimer.

(21) Appl. No.: 11/518,456

(22) Filed: Sep. 8, 2006

(65) Prior Publication Data

US 2007/0185361 A1 Aug. 9, 2007

Related U.S. Application Data

(63) Continuation-in-part of application No. 11/346,651, filed on Feb. 3, 2006, now Pat. No. 7,687,672.

(51) Int. Cl.
*C07C 2/22* (2006.01)

(52) U.S. Cl. ........ 585/512; 585/502; 585/510; 585/511; 585/513; 585/520; 585/521; 585/522; 585/324; 585/326; 585/329

(58) Field of Classification Search .................. 585/511, 585/512, 513, 517; 422/134
See application file for complete search history.

(56) References Cited

U.S. PATENT DOCUMENTS

| | | |
|---|---|---|
| 3,300,458 A | 1/1967 | Manyik et al. |
| 3,333,016 A | 7/1967 | Schultz |
| 4,472,525 A | 9/1984 | Singleton |
| 4,511,746 A | 4/1985 | Miller |
| 4,668,838 A | 5/1987 | Briggs |
| 4,689,437 A | 8/1987 | Murray |
| 4,777,315 A | 10/1988 | Levine et al. |
| 4,853,356 A | 8/1989 | Briggs |
| 5,000,840 A | 3/1991 | Anthes et al. |

(Continued)

FOREIGN PATENT DOCUMENTS

CA 2087578 7/1994

(Continued)

OTHER PUBLICATIONS

J. Fair, "Distillation" in Kirk-Othmer Encyclopedia of Chemical Technology, John Wiley, 1993, posted on-line Aug. 17, 2001.*

(Continued)

*Primary Examiner* — Glenn A Caldarola
*Assistant Examiner* — Bradley Etherton

(57) ABSTRACT

The present invention relates to an in-line method for generating comonomer from monomer, such as ethylene. The comonomer generated is directly transported, without isolation or storage, to a polyethylene polymerization reactor. The in-line method includes the steps of providing an in-line comonomer synthesis reactor and a downstream gas/liquid phase separator prior to the polymerization reactor; feeding ethylene monomer and a catalyst in a solvent and/or diluent to the comonomer synthesis reactor; reacting the ethylene monomer and the catalyst in solvent and/or diluent under reaction conditions to produce an effluent stream including ethylene monomer and comonomer; passing the effluent stream from the comonomer synthesis reactor to the downstream gas/liquid phase separator to separate a gas stream from a bottom stream, wherein the gas stream is a mixture of ethylene monomer and comonomer; and passing the gas stream to the polymerization reactor to provide the necessary comonomer input.

32 Claims, 10 Drawing Sheets

In-Line Process for Comonomer Generation

U.S. PATENT DOCUMENTS

| | | | |
|---|---|---|---|
| 5,137,994 | A | 8/1992 | Goode et al. |
| 5,198,563 | A | 3/1993 | Reagen et al. |
| 5,376,612 | A | 12/1994 | Reagen et al. |
| 5,382,738 | A | 1/1995 | Reagen et al. |
| 5,438,027 | A | 8/1995 | Reagen et al. |
| 5,439,862 | A | 8/1995 | Kemp |
| 5,451,645 | A | 9/1995 | Reagen et al. |
| 5,491,272 | A | 2/1996 | Tanaka et al. |
| 5,523,507 | A | 6/1996 | Reagen et al. |
| 5,541,270 | A | 7/1996 | Chinh et al. |
| 5,543,375 | A | 8/1996 | Lashier et al. |
| 5,550,305 | A | 8/1996 | Wu |
| 5,557,026 | A | 9/1996 | Tanaka et al. |
| 5,563,312 | A | 10/1996 | Knudsen et al. |
| 5,637,660 | A | 6/1997 | Nagy et al. |
| 5,668,249 | A | 9/1997 | Baardman et al. |
| 5,731,487 | A | 3/1998 | Tamura et al. |
| 5,744,677 | A | 4/1998 | Wu |
| 5,750,816 | A | 5/1998 | Araki et al. |
| 5,750,817 | A | 5/1998 | Tanaka et al. |
| 5,763,723 | A | 6/1998 | Reagen et al. |
| 5,811,618 | A | 9/1998 | Wu |
| 5,814,575 | A | 9/1998 | Reagen et al. |
| 5,853,551 | A | 12/1998 | Boucot et al. |
| 5,856,257 | A | 1/1999 | Freeman et al. |
| 5,856,610 | A | 1/1999 | Tamura et al. |
| 5,856,612 | A * | 1/1999 | Araki et al. .................... 585/522 |
| 5,859,303 | A | 1/1999 | Lashier |
| 5,910,619 | A | 6/1999 | Urata et al. |
| 5,919,996 | A | 7/1999 | Freeman et al. |
| 5,968,866 | A | 10/1999 | Wu |
| 6,004,256 | A | 12/1999 | Townsend et al. |
| 6,031,145 | A | 2/2000 | Commereuc et al. |
| 6,103,657 | A | 8/2000 | Murray |
| 6,133,495 | A | 10/2000 | Urata et al. |
| 6,136,748 | A | 10/2000 | Smith |
| 6,137,748 | A | 10/2000 | Murakami |
| 6,265,513 | B1 | 7/2001 | Murray et al. |
| 6,268,447 | B1 | 7/2001 | Murray et al. |
| 6,274,783 | B1 | 8/2001 | Gildert et al. |
| 6,277,841 | B1 | 8/2001 | Rajagopalan et al. |
| 6,303,719 | B1 | 10/2001 | Murray et al. |
| 6,320,002 | B1 | 11/2001 | Murray et al. |
| 6,320,005 | B1 | 11/2001 | Murray |
| 6,337,297 | B1 | 1/2002 | Mimura et al. |
| 6,344,594 | B1 | 2/2002 | Sen et al. |
| 6,380,451 | B1 | 4/2002 | Kreischer et al. |
| 6,399,843 | B1 * | 6/2002 | Koves ........................ 585/510 |
| 6,423,791 | B1 | 7/2002 | Kral |
| 6,437,161 | B1 | 8/2002 | Mihan et al. |
| 6,455,648 | B1 | 9/2002 | Freeman et al. |
| 6,489,263 | B2 | 12/2002 | Murray et al. |
| 6,521,806 | B1 | 2/2003 | Tamura et al. |
| 6,559,091 | B1 * | 5/2003 | Moody et al. ................. 502/167 |
| 6,583,083 | B2 | 6/2003 | Murray et al. |
| 6,610,627 | B2 | 8/2003 | Murray |
| 6,610,805 | B1 | 8/2003 | Guram et al. |
| 6,706,829 | B2 | 3/2004 | Boussie et al. |
| 6,713,577 | B2 * | 3/2004 | Boussie et al. ................. 526/161 |
| 6,727,361 | B2 | 4/2004 | LaPointe et al. |
| 6,750,345 | B2 | 6/2004 | Boussie et al. |
| 6,800,702 | B2 * | 10/2004 | Wass ........................ 526/124.3 |
| 6,828,269 | B2 | 12/2004 | Commereuc et al. |
| 6,828,397 | B2 | 12/2004 | Boussie et al. |
| 6,844,290 | B1 | 1/2005 | Maas et al. |
| 6,844,920 | B2 | 1/2005 | Louellau |
| 6,900,152 | B2 | 5/2005 | Yoshida et al. |
| 7,214,842 | B2 | 5/2007 | Mihan et al. |
| 7,638,670 | B2 * | 12/2009 | McConville et al. ......... 585/513 |
| 7,638,671 | B2 * | 12/2009 | McConville et al. ......... 585/513 |
| 7,687,672 | B2 * | 3/2010 | Buchanan et al. ............ 585/326 |
| 2001/0034297 | A1 | 10/2001 | Murray et al. |
| 2002/0035029 | A1 | 3/2002 | Yoshida et al. |
| 2002/0065379 | A1 | 5/2002 | Murray |
| 2002/0137845 | A1 | 9/2002 | Boussie et al. |
| 2002/0142912 | A1 | 10/2002 | Boussie et al. |
| 2002/0147288 | A1 | 10/2002 | Boussie et al. |
| 2002/0153697 | A1 | 10/2002 | Amirola |
| 2002/0156279 | A1 | 10/2002 | Boussie et al. |
| 2002/0173419 | A1 | 11/2002 | Boussie et al. |
| 2002/0177711 | A1 | 11/2002 | LaPointe et al. |
| 2002/0183574 | A1 | 12/2002 | Dixon et al. |
| 2003/0130551 | A1 | 7/2003 | Drochon et al. |
| 2003/0149198 | A1 | 8/2003 | Small et al. |
| 2003/0153697 | A1 | 8/2003 | Boussie et al. |
| 2003/0166456 | A1 | 9/2003 | Wass |
| 2004/0122247 | A1 | 6/2004 | Boussie et al. |
| 2004/0122271 | A1 | 6/2004 | Van Zon et al. |
| 2004/0228775 | A1 * | 11/2004 | Ewert et al. .................. 422/131 |
| 2004/0236163 | A1 | 11/2004 | Ewert et al. |
| 2005/0020788 | A1 | 1/2005 | Wass |
| 2005/0020866 | A1 | 1/2005 | Kobayashi et al. |
| 2005/0113524 | A1 | 5/2005 | Stevens et al. |
| 2005/0197521 | A1 | 9/2005 | Kreischer |
| 2006/0094839 | A1 | 5/2006 | Diamond et al. |
| 2006/0094867 | A1 | 5/2006 | Diamond et al. |
| 2006/0173226 | A1 | 8/2006 | Blann et al. |
| 2006/0211903 | A1 | 9/2006 | Blann et al. |
| 2006/0229480 | A1 | 10/2006 | Blann et al. |
| 2006/0247339 | A1 | 11/2006 | Harashina et al. |
| 2006/0247399 | A1 | 11/2006 | McConville et al. |
| 2006/0247483 | A1 | 11/2006 | McConville et al. |
| 2006/0293546 | A1 | 12/2006 | Nabika |
| 2007/0027350 | A1 | 2/2007 | Nabika |
| 2007/0049781 | A1 * | 3/2007 | Brown et al. ................. 585/517 |
| 2007/0185358 | A1 | 8/2007 | Buchanan et al. |
| 2007/0185364 | A1 | 8/2007 | Buchanan et al. |

FOREIGN PATENT DOCUMENTS

| | | |
|---|---|---|
| CA | 2115639 | 9/1994 |
| CN | 1256968 | 6/2000 |
| EP | 237 079 | 7/1990 |
| EP | 416 304 | 3/1991 |
| EP | 537 609 | 4/1993 |
| EP | 608 447 | 8/1994 |
| EP | 614 865 | 9/1994 |
| EP | 622 347 | 11/1994 |
| EP | 668 106 | 8/1995 |
| EP | 699 648 | 3/1996 |
| EP | 706 983 | 4/1996 |
| EP | 780 353 | 6/1997 |
| EP | 889 061 | 1/1999 |
| EP | 993 464 | 4/2000 |
| EP | 1 110 930 | 6/2001 |
| EP | 1 308 450 | 5/2003 |
| EP | 1 364 974 | 11/2003 |
| EP | 1 607 415 | 12/2005 |
| GB | 2 298 864 | 9/1996 |
| JP | 07010780 | 1/1995 |
| JP | 06515873 | 3/1995 |
| JP | 07215896 | 8/1995 |
| JP | 07267881 | 10/1995 |
| JP | 09020692 | 1/1997 |
| JP | 09020693 | 1/1997 |
| JP | 09268133 | 10/1997 |
| JP | 09268134 | 10/1997 |
| JP | 09268135 | 10/1997 |
| JP | 10-007712 | 1/1998 |
| JP | 10007593 | 1/1998 |
| JP | 10007594 | 1/1998 |
| JP | 10007595 | 1/1998 |
| JP | 10036431 | 2/1998 |
| JP | 10036432 | 2/1998 |
| JP | 10045638 | 2/1998 |
| JP | 10087518 | 4/1998 |
| JP | 11092407 | 4/1999 |
| JP | 11092408 | 4/1999 |
| JP | 11222445 | 8/1999 |
| JP | 10007712 | 1/2000 |
| JP | 2000176291 | 6/2000 |
| JP | 2000202299 | 7/2000 |
| JP | 2000212212 | 8/2000 |
| JP | 2007-010780 | 1/2001 |
| JP | 2001009290 | 1/2001 |
| JP | 2001187345 | 7/2001 |
| JP | 2002045703 | 2/2002 |
| JP | 2002066329 | 3/2002 |

| | | |
|---|---|---|
| JP | 2002102710 | 4/2002 |
| JP | 2002172327 | 6/2002 |
| JP | 2002200429 | 7/2002 |
| JP | 2002205960 | 7/2002 |
| JP | 2002233765 | 8/2002 |
| JP | 3351068 | 11/2002 |
| JP | 2003071294 | 3/2003 |
| JP | 3540827 | 7/2004 |
| JP | 3540828 | 7/2004 |
| JP | 3577786 | 10/2004 |
| WO | WO 97/37765 | 10/1997 |
| WO | WO 99/01460 | 1/1999 |
| WO | WO 99/19280 | 4/1999 |
| WO | WO 00/37175 | 6/2000 |
| WO | WO 00/50470 | 8/2000 |
| WO | WO 01/10876 | 2/2001 |
| WO | WO 01/47839 | 7/2001 |
| WO | WO 01/48028 | 7/2001 |
| WO | WO 01/68572 | 9/2001 |
| WO | WO 01/83447 | 11/2001 |
| WO | WO 02/04119 | 1/2002 |
| WO | WO 02/38628 | 5/2002 |
| WO | WO 02/46249 | 6/2002 |
| WO | WO 02/066404 | 8/2002 |
| WO | WO 02/066405 | 8/2002 |
| WO | WO 02/083306 | 10/2002 |
| WO | WO 03/004158 | 1/2003 |
| WO | WO 03/053890 | 7/2003 |
| WO | WO 03/053891 | 7/2003 |
| WO | WO 2004/056477 | 7/2004 |
| WO | WO 2004/056478 | 7/2004 |
| WO | WO 2004/056479 | 7/2004 |
| WO | WO 2004/056480 | 7/2004 |
| WO | WO 2004/083263 | 9/2004 |
| WO | WO 2005/123633 | 12/2005 |
| WO | WO 2005/123884 | 12/2005 |
| WO | WO 2006/096881 | 9/2006 |
| WO | WO 2007/007272 | 1/2007 |

OTHER PUBLICATIONS

S. Walas, "Chemical Reactors" in Perry's Chemical Engineers' Handbook (7th edition, 1997), Perry, R.H.; Green, D.W. editors, pp: 23-36-23-37, McGraw-Hill. Online version available at: http://knovel.com.*

J. Dixon, et. al. "Advances in Selective Ethylene Trimerization—A Critical Overview," in J. Organomet. Chem., 689 (2004), 3641-3668.*

Seador, et al., "Distillation" in Perry's Chemical Engineer's Handbook, John Wiley (1997), posted on-line Mar. 1, 2001.*

Dixon, et al., "Advances in Selective Ethylene Trimerization—A Critical Overview," in J. Organomet. Chem., 689 (2004), 3641-3668.*

Gokel, G. W., ed., Lange's Handbook of Organic Chemistry, McGraw-Hill, 2004, 2nd edition, available on-line at www.knovel.com.*

A. Ranwell et al., "Potential Application of Ionic Liquids for Olefin Oligomerization," ACS Symposium Series, Chapter 12, 2002, 818, pp. 147-160.

R.D. Kohn et al., 1,3,5-Triazacyclohexane Complexes of Chromium as Homogeneous Model Systems for the Phillips Catalyst, ACS Symposium Series, 2003, 857, pp. 88-100.

K.R. Dunbar et al., "Structure of [HTMPP]$_3$W$_2$CL$_9$[HTMPP=Tris(2,4,6-trimethoxyphenyl)-phosphonium]," Acta Cryst., 1991, C47, pp. 23-26.

D.H. Morgan et al., "The Effect of Aromatic Ethers on the Trimerisation of Ethylene using a Chromium Catalyst and Aryloxy Ligands," Adv. Synth. & Catalysis, 2003, 345, pp. 939-942.

Y.Yang et al., "Roles of chloro compound in homogeneous [Cr(2-ethylhexanoate)$_3$/2,5-dimethylpyrrole/triethylaluminum/chloro compound] catalyst system for ethylene trimerization," Applied Catalysis A: General, 2000, 193, pp. 29-38.

H. Mahomed et al., "Ethylene trimerisation catalyst based on substituted cyclopentadienes," Applied Catalysis A: General, 2003, 255, pp. 355-359.

Kohn et al., Triazacyclohexane complexes of chromium as highly active homogeneous model sytstems for the Philips catalyst, Chem. Commun., 2000, pp. 1927-1928.

A. Carter et al., "High activity ethylene trimerisation catalysts based on diphosphine ligands," Chem. Commun., 2002, pp. 858-859.

D.S. McGuinness et al., "Novel Cr-PNP complexes as catalysts for the trimerisation of ethylene," Chem. Commun. 2003, pp. 334-335.

C.N. Nenu et al., "Single-site heterogeneous Cr-based catalyst for the selective trimerisation of ethylene," Chem. Commun., 2005, pp. 1865-1867.

K. Blann et al., "Highly selective chromium-based ethylene trimerisation catalysts with bulky diphosphinoamine ligands," Chem. Commun., 2005, pp. 620-621.

M.J. Overett et al., "Ethylene trimerisation and tetramerisation catalysts with polar-substituted diphosphinoamine ligands," Chem. Commun., 2005, pp. 622-624.

Hecheng Shuzhi Ji Suliao, China Synthetic Resin and Plastics, 2001, 18(2), 23-25, 43.

T. Imamoto et al., "Synthesis and reactions of Optically Pure Cyclohexyl (o-methoxyphenyl)phosphine-Borane and t-Butyl-(o-methoxyphenyl)phosphine-Borane," Heteroatom Chemistry, 1993, vol. 4, No. 5, pp. 475-486.

N.J. Robertson et al., "Chromium(II) and Chromium (III) Complexes Supported by Tris(2-pyridylmethyl)amine: Synthesis, Structures, and Reactivity," Inorg. Chem., 42, pp. 6876-6885 (2003).

L. Hirsivaara et al., "M(CO)$_6$ (M=Cr, Mo, W) derivatives of (o-anisyl)diphenylphosphine, bis(o-anisyl)phenylphosphine tris(o-anisyl)phosphine and (p-anisyl)bis(o-anisyl)phosphine," Inorganica Chimica Acta, 2000, 307, pp. 47-56.

D.S. McGuinness et al., "First Cr(III)-SNS Complexes and Their Use as Highly Efficient Catalysts for the Trimerization of Ethylene to 1-Hexene," J. Am .Chem. Soc., 2003, 125, pp. 5272-5273.

C. Andes et al., "New Tantalum-based Catalyst System for the Selective Trimerization of Ethene to 1-Hexene," J. Am. Chem. Soc., 2001, 123, pp. 7423-7424.

T.Agapie et al., "Mechanistic Studies of the Ethylene Trimerization Reaction with Chromium-Diphosphine Catalysts: Experimental Evidence for a Mechanism Involving Metallacyclic Intermediates," J. Am. Chem. Soc., 126, 2004, pp. 1304-1305.

A. Bollmann et al., "Ethylene Tetramerization: A New Route to Produce 1-Octene in Exceptionally High Selectivities," J. Am. Chem. Soc., 126, 2004, pp. 14712-14713.

A. Ariffin et al., "The asymmetric synthesis of phosphorus- and sulfur-containing tricarbonyl(n$^6$-arene) chromium complexes using the chiral base approach," J. Chem. Soc., Perkin Trans., 1, 1999, pp. 3177-3189.

T. Monoi et al., "Silica-supported Cr[N(SiMe$_3$)$_2$]$_3$/ isobutylalumoxane catalyst for selective ethylene trimerization," Journal of Mol. Catalysis A: Chemical, 187, 2002, pp. 135-141.

J.T. Dixon et al., "Advances in selective ethylene trimerisation—a critical overview," Jrnl. of Organometallic Chem., 689, 2004, pp. 3641-3668.

R.M. Manyik et al., "A Soluble Chromium-Based Catalyst for Ethylene Trimerization and Polymerization," Journal of Catalysts, 1977, 47, pp. 197-209.

L. Hirsivaara et al., "Organometallic derivatives of multidentate phosphines [o-(methylthio)phenyl]diphenylphosphine and bis(o-(methylthio)phenyl(phenylphosphine: preparation and characterization of group 6 metal carbonyl derivatives," Jrnl. of Organometallic Chem., 579, 1999, pp. 45-52.

J. Pietsch et al., "Koordinationschemie funktioneller Phosphine II. Carbonyl(nitrosyl) wolfram-Komplexe mit 2-Diphenylphosphphinoanisol sowie 2-Diphenylphosphinoanilid, -benzoat und -phenolat als Liganden," Journal of Organometallic Chemistry, 495, 1995, pp. 113-125.

L. Dahlenburg et al., "Koordinationschemie funktioneller Phosphane VIII. Tetracarbonylkomplexe des Wolframs und Molybdans mit 2-(Diphenylphosphanyl)anilin-Liganden," Journal of Organometallic Chemistry, 585, 1999, pp. 225-233.

D. de Wet-Roos et al., "Homogeneous Tandem Catalysis of Bis(2-decylthioethyl)amine-Chromium Trimerization Catalyst in Combination with Metallocene Catalysts," Macromolecules, 2004, 37, pp. 9314-9320.

R. Blom et al., "1,3,5-Triazacyclohexane Complexes of Chromium as Homogeneous Model Systems for the Phillips Catalyst," Organometallic Catalysts and Olefin Polymerization, 2001, pp. 147-155.

K. Burgess, Stereochemically Matched (and Mismatched) Bisphosphine Ligands: DIOP-DIPAMP Hybrids, Organometallics, 1992, 11, pp. 3588-3600.

K.R. Dunbar et al., Carbon Monoxide Reactions of the Fluxional Phosphine Complex $(n^3-PR_3)Mo(CO)_3$ (R = 2,4,6-Trimethoxyphenyl), Organometallics, 1994, 13, pp. 2713-2720.

G. Boni et al., "Heterobimetallic Dibridged Complexes [$Cp_2Ta(u-CO)(u-PMe_2)M'(CO)_4$] (M' = Cr, W): Synthesis and Reactivity toward Two-Electron Donor Ligands L (L = $PR_3$, $Me_2P(CH_2)nPMe_2$, CNR)," Organometallics, 1995, 14, pp. 5652-5656.

T. Agapie et al.; "A Chromium-Diphosphine System for Catalytic Ethylene Trimerization: Synthetic and Structural Studies of Chromium Complexes with a Nitrogen-Bridged Diphosphine Ligand with ortho-Methoxyaryl Substituents"; Organometallics, 25; 2006, pp. 2733-2742.

R.L. Wife et al., "Phosphine Oxide Anions in the Synthesis of Phosphine Ligands," Synthesis, 1983, pp. 71-73.

P.J.W. Deckers et al., "Catalytic Trimerization of Ethene with Highly Active Cyclopentadienyl-Arene Titanium Catalysts," Organometallics, 2002, 21, pp. 5122-5135.

S. Naqvi, "1-Hexene From Ethylene by the Phillips Trimerization Technology," available on-line at http://www.sriconsulting.com/PEP/Reports/Phase_95/RW95-1-1/RW95-1-8.html, Dec. 1997.

R. Agrawal "*More Operable Fully Thermally Coupled Distillation Column Configurations for Multicomponent Distillation*", Transactions of the Institution of Chemical Engineers, 1999, 77(A) pp. 543-553.

Y. T. Shah, et al. "*Design Parameters Estimations for Bubble Column Reactors*", American Institute of Chemical Engineers' Journal, 1982, vol. 28 No. 3, pp. 353-379.

K.M. Sundaram, et al. "*Ethylene*" Kirk-Othmer Encyclopedia of Chemical Technology, John Wiley, 2001, vol. 10, pp. 593-632, posted on-line Apr. 16, 2001.

B. L. Small et al., "*New Chromium Complexes for Ethylene Oligomerization: Extended Use of Tridentate Ligands in Metal-Catalyzed Olefin Polymerization*", Macromolecules, 2004, vol. 37, No. 12, pp. 4375-4386.

"*Chemical Reactors*" Perry's Chemical Engineers' Handbook 7th Edition, 1997, pp. 26-36 and 23-40.

\* cited by examiner

In-Line Process for Comonomer Generation

Fixed Bed Reactors for In-Line Comonomer Generation with Catalyst in Tubes with Coolant Fixed Bed Reactors for In-Line Comonomer Generation with Cold Shot Cooling

A23

A24

A25

A26

A27

A28

A29

A30

A31

A32

IN-LINE PROCESS FOR GENERATING COMONOMER

PRIORITY CLAIM

This invention is a continuation in part of U.S. Ser. No. 11/346,651, filed Feb. 3, 2006 now U.S. Pat. No. 7,687,672 and assigned to ExxonMobil Research and Engineering.

FIELD OF THE INVENTION

The present invention relates to the field of chemical reaction and separation processes. It more particularly relates to an improved process for generating linear alpha olefin comonomers from monomer from specific catalysts and or catalyst systems.

BACKGROUND

Olefin polymerization, especially ethylene polymerization, can benefit from the addition of longer-chain comonomers, such as 1-hexene, and 1-octene, to produce linear low density polyethylene (LLDPE). LLDPE produced from 1-hexene and 1-octene accounts for a large percentage of the polyethylene resin market. In general, polyethylene plants buy hexene and octene, which are produced in separate plants that typically produce a range of even-numbered alpha olefins from ethylene. It can be expensive to purchase these materials, and they add to the complexity of storage and handling. An attractive alternative is to make the comonomer directly from the ethylene, if this can be done cleanly and economically. It would be perhaps most economical to do this in-situ in the polymerization reactor by altering the catalyst, however this is very difficult.

The review article "Advances in selective ethylene trimerisation—a critical review" by Dixon et al. (J. Organometallic Chemistry 689 (2004) 3641-3668), herein incorporated by reference in its entirety, describes many different catalysts for trimerization. These catalyst systems contain chromium, and with particular ligands, such as aromatic species (e.g. pyrrolyl) or multidentate heteratomic species. The chromium catalysts are typically activated by alkylaluminum and/or alkylaluminoxane activators. The article also describes group 4 and 5 early transition metals, such as Zr, V, Ta and Ti, and group 8 late transition metals, such as Ni, for showing some activity in trimerization.

Phillips has developed and patented chromium-based catalysts that are selective towards making 1-hexene from ethylene. The major byproduct appears to be 1-decene. SR1 Consulting PEP Review 95-1-8 entitled "1-Hexene From Ethylene By the Phillips Trimerization Technology," available on-line at http://www.sriconsulting.com/PEP/Reports/Phase_95/RW95-1-8/RW95-1-8.html, herein incorporated by reference in its entirety, describes the Phillips standalone process for making 1-hexene based on Phillips trimerization technology. In this process, ethylene and a homogeneous catalyst in a solvent and or diluent are fed to a reactor. The reactor is a stirred tank with heat removal coils. This reactor operates at 115 deg. C. and 49 kg/cm2 (~700 psia), and converts about 75% of the ethylene fed. This reactor is 42,300 gal (5655 ft3). A spare reactor is provided, since waxy buildup on the cooling coils may necessitate lengthy shutdowns for cleaning. The feed is approximately 29,000 lb/hr cyclohexane solvent (with catalyst) plus 36,000 lb/hr ethylene (27,000 fresh feed and 9,000 recycle). It is estimated that the resident time in the reactor is on average 4 to 5 hours. Selectivity in the Phillips process by weight is about 93% to 1-hexene, 1% to other C6s, 1% to octenes, and 5% to decenes. The effluent from the reactor is contacted with octanol to kill the catalyst from further reaction. The effluent then goes to an ethylene column, where unconverted ethylene is taken overhead and recycled to the reactor. Because ethylene is so volatile, an expensive cryogenic column must be used. Four more distillation columns follow to remove hexene, cyclohexane solvent, octene, and decene. Some of these are run under vacuum, which again makes for expensive hardware and operations. The bottoms from the decene tower is a small stream containing mainly octanol and deactivated catalyst. This stream is treated with caustic and then with acid to remove the catalyst by precipitation and by solution in an aqueous phase, which is separated from the organic phase containing the octanol. Octanol may then be recycled.

U.S. Pat. No. 5,382,738 to Reagen et al., herein incorporated by reference in its entirety, discloses catalyst systems comprising inorganic oxides, modified with a metal alkyl and an unsaturated hydrocarbon, which can be used to support a metal source, such as, for example, chromium, and a pyrrole-containing compound. The resultant catalyst systems can be used to oligomerize and/or trimerize olefins.

U.S. Pat. No. 5,451,645 to Reagen et al., herein incorporated by reference in its entirety, discloses novel chromium-containing compounds prepared by forming a mixture of a chromium salt, a metal amide, and an ether. These novel chromium-containing, or chromium pyrrolide compounds, with a metal alkyl and an unsaturated hydrocarbon, can be used as a cocatalyst system in the presence of an olefin polymerization catalyst system to produce a comonomer in-situ.

U.S. Pat. No. 5,523,507 to Regen et al., herein incorporated by reference in its entirety, discloses novel chromium-containing compounds prepared by forming a mixture of the chromium salt, a metal amide, and an ether either supported or unsupported. These novel chromium-containing compounds are activated by non-hydrolyzed alkyl aluminum compound and a Lewis acid.

U.S. Pat. No. 5,543,375 to Lashier et al., herein incorporated by reference in its entirety, discloses a process to stabilize and/or reactivate an olefin production catalyst system which comprises contacting an olefin production catalyst system, either before or after use, with an aromatic compound, but prior to contacting the system with a reactant.

U.S. Pat. No. 5,563,312 to Knudsen et al., herein incorporated by reference in its entirety, discloses a process to stabilize and/or reactivate an olefin production catalyst system which comprises contacting an olefin production catalyst system, either before or after use, with an aromatic compound.

U.S. Pat. No. 5,859,303 to Lashier, herein incorporated by reference in its entirety, discloses a process in which the solvent is the product of the olefin oligomerization process. This novel process uses a catalyst essentially comprising a chromium compound or chromium salt, a pyrrole-containing compound, and an alkyl compound.

European Patent No. 0 668 106 to Freeman et al., herein incorporated by reference in its entirety, discloses a process which will effectively deactivate, inhibit, and/or "kill" an olefin production catalyst, and halt polymer production in an olefin production process. It further provides for a process which can remove an olefin production catalyst from the product stream, and recover catalyst by-products for recycle, and/or recovery.

PCT publication WO 99/19280A1 to Woodard et al., herein incorporated by reference in its entirety, discloses a process in which olefins are trimerized in the presence of a catalyst system comprising a chromium source, a pyrrole containing compound and a metal alkyl. The process is preformed in a reactor and provides for a separator for collection of the desired products.

PCT publications WO 2004/056478 to Blann et al. and WO 2004/056479 to Blann et al., both hereby incorporated by reference in their entirety, disclose processes and catalysts to prepare an olefinic stream with more than 30% of 1-octene. The catalysts for this system are those that contain chromium or a chromium salt and a heteroatomic ligand A need exists for an improved process to generate comonomer in a pre-reactor immediately before the polymerization reactor without isolation of the comonomer. More particularly, a need exists for a reaction/separation process to generate 1-hexene from ethylene immediately before the LLDPE polymerization reactor with no isolation or storage of the hexene produced. With regard to specific oligomerization catalyst systems, particularly ethylene trimerization systems, the following references are of interest: U.S. Pat. No. 4,668,838; U.S. Pat. No. 5,137,994; U.S. Pat. No. 5,198,563; U.S. Pat. No. 5,382,738; U.S. Pat. No. 5,438,027; U.S. Pat. No. 5,523,507; U.S. Pat. No. 5,543,375; U.S. Pat. No. 5,856,257; EP 0 416 304 B1; EP 0 608 447 B1; EP 0 780 353 B1; CA 2,087,578; U.S. Pat. No. 5,491,272; U.S. Pat. No. 5,750,817; U.S. Pat. No. 6,133,495; U.S. Pat. No. 5,750,816; U.S. Pat. No. 5,856,612; U.S. Pat. No. 5,910,619; EP 0 537 609; CA 2,115,639; EP 0 614 865 B1; EP 0 699 648 B1; WO03/053890; McGuinness et al., *J. Am. Chem. Soc.* 125, 5272-5273, (2003); WO02/083306A2; WO03/004158A2; U.S. Pat. No. 5,968,866; WO02/04119A1 (and related U.S. Pat. No. 6,800,702, U.S. 2003/166456, and U.S. 2005/020788); *J. Am. Chem. Soc.* 123, 7423-7424 (2001); WO01/68572A1; WO02/066404A1; WO04/056477; WO04/056478; WO04/056479; WO04/056480; EP 1 110 930 A1; U.S. Pat. No. 3,333,016; U.S. Pat. No. 5,439,862; U.S. Pat. No. 5,744,677; U.S. Pat. No. 6,344,594; and U.S. Pat. App. Pub. No. 2002/0035029A1; Carter et al., *Chem. Commun.*, 2002, pp. 858-859; JP 2001187345A2; JP 2001187345A2.

Likewise additional references regarding ethylene trimerization catalysts include: WO01/10876, WO97/37765, EP 1 110 930 A1, U.S. Pat. No. 3,333,016, U.S. Pat. No. 5,439,862, U.S. Pat. No. 5,744,677, U.S. Pat. No. 6,344,594, U.S. Pat. No. 4,689,437, U.S. Pat. No. 4,472,525, U.S. Pat. No. 5,668,249, U.S. Pat. No. 5,856,610, U.S. Pat. No. 3,300,458, U.S. Pat. App. Pub. No. 2002/0035029A1, *Journal of Organometallic Chemistry* 579 (1999) 45-52, *Organometallics* 1992, 11 3588-3600, *Organometallics* 1995, 14, 5652-5656, *J. Chem. Soc., Perkin Trans.* 1, 1999, 3177-3189, *Organometallics* 1994, 13, 2713-2720, *Journal of Organometallic Chemistry*, Volume 585, Issue 2, 15 Aug. 1999, pgs 225-233, *Acta Cryst.* (1991). C47, 23-26, *Journal of Organometallic Chemistry*, Vol 495, No. 1, 14 Jun. 1995, pgs 113-125, *Inorg. Chim. ACTA* (2000), 307(1-2), 47-56. *Chem. Commun.* 2005, 620-621, *Chem. Commun.* 2005, 622-624, *Chem. Commun.* 2005, 1865-1867, *J. Am. Chem. Soc.* 2004, 126, 14712-14713, *J. Am. Chem. Soc.* 2004, 126, 1304-1305, *Macromolecules*, 2004, 37, 9314-9320, *Journal of Organometallic Chemistry*, 2004, 689, 3641-3668, *Heteroatom* Chemistry, 1993, 4, 475-486; Synthesis, 1983, 1, 71-73; U.S. Pat. No. 6,800,702; *Chem. Commun.*, 2002, 8, 858-859; *PERP Report*, Nexant/Chem Systems, 2004, 57-60; *Dangadi Shiyou Shihu*, 2002, 10, 25-29; *ACS Symposium Series*, 2002, 818, 147-160; *Journal of Organometallic Chemistry*, 2004689, 3641-3668; U.S. Pat. No. 4,668,838; U.S. Pat. No. 4,777,315; U.S. Pat. No. 4,853,356; U.S. Pat. No. 5,744,677; EP-608447; U.S. Pat. No. 5,557,026; JP06515873; U.S. Pat. No. 5,750,817; U.S. Pat. No. 5,731,487; EP-622347; U.S. Pat. No. 5,376,612; U.S. Pat. No. 5,382,738; JP3540827 B2; JP3540828 B2; JP3351068 B2; U.S. Pat. No. 5,563,312; JP07215896; JP07267881; U.S. Pat. No. 6,521,806; EP-706983; U.S. Pat. No. 5,523,507; U.S. Pat. No. 5,910,619; U.S. Pat. No. 5,550,305; U.S. Pat. No. 5,750,816; GB2298864; JP3577786 B2; JP09020692; JP09020693; U.S. Pat. No. 5,859,303; U.S. Pat. No. 5,856,612; U.S. Pat. No. 6,133,495; JP09268133; JP09268134; JP09268135; JP10007593; JP10007594; JP10007595; JP10036431; JP10036432; JP10045638; JP10087518; U.S. Pat. No. 5,763,723; U.S. Pat. No. 5,811,618; U.S. Pat. No. 5,814,575; U.S. Pat. No. 6,031,145; U.S. Pat. No. 5,856,257; JP111092407; JP111092408; U.S. 2004228775; U.S. Pat. No. 5,919,996; JP11222445; U.S. Pat. No. 5,968,866; U.S. Pat. No. 6,610,805; CN1256968; JP2000176291; JP2000202299; U.S. Pat. No. 6,337,297; JP2000212212; JP2001009290; U.S. 2002183574; U.S. Pat. No. 6,828,269; WO200147839 U.S. Pat. No. 6,455,648; WO200183447; JP2002045703; JP2002066329; JP2002102710; U.S. 2002035029; JP2002172327; JP2002200429; JP2002233765; WO200283306; WO2003004158; JP2002205960; U.S. 2003130551; WO2003053890; WO2003053891; JP2003071294; U.S. 2003149198; U.S. 2004122271; WO2004056479; WO2004056478; WO2004083263; *Journal of Catalysis*, 1977, 47, 197-209; *J. Am. Chem. Soc.*, 1989, 11, 674-675; *Applied Catalysis, A* (General) 2000, 193, 29-38; *Hecheng Shuzhi Ji Suliao*, 2001, 18, 23-25, 43; *Organometallic Catalysts and Olefin Polymerization*, 2001, 147-155; *J. Mol. Catalysis. A: Chemical* (2002), 187, 135-141; *J. Am. Chem. Soc.*, 2002, 125, 5272-5273; *Chem. Commun.* 2003, 3, 334-335; *Beijing Huagong Daxue Xuebao, Ziran Kexueban*, 2003, 30, 80-82; *Adv. Synth. & Catalysis*, 2003, 345, 939-942; *Applied Catalysis, A: General*, 2003, 255, 355-359; *J. Am. Chem. Soc.* 2004, 126, 1304-1305; *ACS Symposium Series*, 2003, 857 (Beyond Metallocenes), 88-100; and *J. Am. Chem. Soc.*, 2004, 126, 14712-14713. Although the catalyst compositions in each of the above described references may be useful for the trimerization of ethylene, there remains a desire to improve the performance of olefin oligomerization catalysts from the standpoint of productivity and selectivity for oligomers such as 1-hexene or 1-octene, particularly where use in a commercial process, particularly an in-line process, is concerned.

Several pyridyl amine catalyst complexes have been disclosed for the polymerization or copolymerization of ethylene, propylene, isobutylene, octene, and styrene by Symyx Technologies, Inc. in U.S. Pat. Nos. 6,713,577, 6,750,345, 6,706,829, 6,727,361, and 6,828,397. Pyridyl amines were also disclosed in U.S. Pat. Nos. 6,103,657 and 6,320,005, assigned to Union Carbide Chemical and Plastics Technology Corporation, in which zirconium was used as the metal center, and the catalyst complex was used to polymerize alpha-olefins, and in U.S. Pat. No. 5,637,660, assigned to Lyondell Petrochemical Company, which also describes Group 4 complexes of pyridyl amine ligands. Robertson et al., *Inorg. Chem.* 42, pp 6875-6885 (2003), discloses chromium complexes of tris(2-pyridylmethyl)amine for ethylene polymerization.

This invention also relates to U.S. patent application Ser. Nos. 60/611,943, 11/232,982 and 11/233,227.

This invention also relates to U.S. Ser. No. 60/841,226, filed Aug. 30, 2006 assigned to ExxonMobil Chemical Patents Inc.; U.S. Ser. No. 11/371,614, filed Mar. 9, 2006, assigned to ExxonMobil Chemical Patents Inc.; and U.S. Ser. No. 11/371,983, filed Mar. 9, 2006, assigned to ExxonMobil Chemical Patents Inc.

This invention also relates to U.S. Ser. No. 11/346,651, filed Feb. 3, 2006 and U.S. Ser. No. 11/346,652, filed Feb. 3, 2006, both assigned to ExxonMobil Research and Engineering.

SUMMARY OF THE INVENTION

This invention relates to the oligomerization, and more specifically the trimerization and/or tetramerization of C2 to C12 olefins, preferably alpha-olefins, preferably ethylene using the ligand-metal-precursor-combinations, metal-ligand-complexes, and/or catalyst systems described herein in the unique in-line processes for generating comonomer described herein. Specifically, this invention relates to the trimerizing and/or tetramerizing of ethylene to form 1-hexene and/or 1-octene using the ligand-metal-precursor-combinations, metal-ligand-complexes, and/or catalyst systems described herein in the unique in-line processes for generating comonomer described herein.

It has been discovered that it is possible to generate 1-hexene and other comonomers from ethylene immediately before the polyethylene polymerization reactor with no isolation or storage of the hexene or other comonomer produced.

According to the present disclosure, an advantageous method for generating 1-hexene and other comonomers immediately before a polyethylene polymerization reactor, includes the steps of: providing an in-line comonomer synthesis reactor and a downstream gas/liquid phase separator prior to a polyethylene polymerization reactor; feeding ethylene monomer and a catalyst in a solvent or diluent to the comonomer synthesis reactor; reacting the ethylene monomer and the catalyst in solvent or diluent under reaction conditions to produce an effluent stream comprising ethylene monomer and comonomer selected from the group consisting of 1-hexene, 1-octene; 1-decene and mixtures thereof; passing the effluent stream from the comonomer synthesis reactor to the downstream gas/liquid phase separator to separate a gas stream from a bottoms stream, wherein the gas stream is a mixture of ethylene monomer, and the comonomer; purging from the bottom stream spent catalyst and purge heavies, and recycling the catalyst in solvent and or diluent to the comonomer synthesis reactor; and passing the gas stream to the polyethylene polymerization reactor to provide a comonomer source.

A further aspect of the present disclosure relates to an advantageous method for generating 1-hexene and other comonomers immediately before a polyethylene polymerization reactor, which includes the steps of: providing an in-line comonomer synthesis reactor prior to a polyethylene polymerization reactor, wherein the reactor is a fixed bed type with a catalyst in a fixed position; feeding ethylene monomer to the comonomer synthesis reactor; reacting the ethylene monomer and the catalyst under reaction conditions to produce an effluent stream comprising ethylene monomer and comonomer selected from the group consisting of 1-hexene, 1-octene; 1-decene and mixtures thereof; and directing the effluent stream to the polyethylene polymerization reactor to provide a comonomer source.

Another aspect of the present disclosure relates to an advantageous method for generating 1-hexene and other comonomers immediately before a polyethylene polymerization reactor, which includes the steps of: providing an in-line comonomer synthesis reactor and a downstream gas/liquid phase separator prior to a polyethylene polymerization reactor; feeding ethylene monomer and a catalyst in a solvent or diluent to the comonomer synthesis reactor; reacting the ethylene monomer and the catalyst in solvent or diluent under reaction conditions to produce an effluent stream comprising ethylene monomer and comonomer selected from the group consisting of 1-hexene, 1-octene; 1-decene and mixtures thereof; passing the effluent stream from the comonomer synthesis reactor to the downstream gas/liquid phase separator to separate a gas stream from a bottom stream, wherein the gas stream is a mixture of ethylene monomer, and the comonomer; and transporting without isolation or storage the gas stream to the polyethylene polymerization reactor to provide a comonomer source.

Numerous advantages result from the advantageous method of preparing comonomer from monomer immediately before the polymerization reactor disclosed herein and the uses/applications therefore.

For example, in exemplary embodiments of the present disclosure, the disclosed method for preparing comonomer from monomer immediately before the polymerization reactor provides for substantial capital and operational cost savings over a conventional standalone process for manufacturing comonomer.

In a further exemplary embodiment of the present disclosure, the disclosed method for preparing comonomer from monomer immediately before the polymerization reactor eliminates the need to store or isolate the monomer produced.

In a further exemplary embodiment of the present disclosure, the disclosed method for preparing comonomer from monomer immediately before the polymerization reactor provides for range of catalysts for the oligomerization reaction.

In a further exemplary embodiment of the present disclosure, the disclosed method for preparing comonomer from monomer immediately before the polymerization reactor provides for the capability to produce both hexene and octene through catalyst selection.

In a further exemplary embodiment of the present disclosure, the disclosed method for preparing comonomer from monomer immediately before the polymerization reactor provides for process simplification, and the associated benefits of such.

In a further exemplary embodiment of the present disclosure, the disclosed method for preparing comonomer from monomer immediately before the polymerization reactor provides for continual removal of hexene from the comonomer synthesis reactor zone, which reduces the formation of decene byproduct.

These and other advantages, features and attributes of the disclosed method for preparing comonomer from monomer immediately before the polymerization reactor of the present disclosure and their advantageous applications and/or uses will be apparent from the detailed description which follows, particularly when read in conjunction with the figures appended hereto.

BRIEF DESCRIPTION OF THE DRAWINGS

To assist those of ordinary skill in the relevant art in making and using the subject matter hereof, reference is made to the appended drawings, wherein.

DETAILED DESCRIPTION OF THE INVENTION

Figure 1:
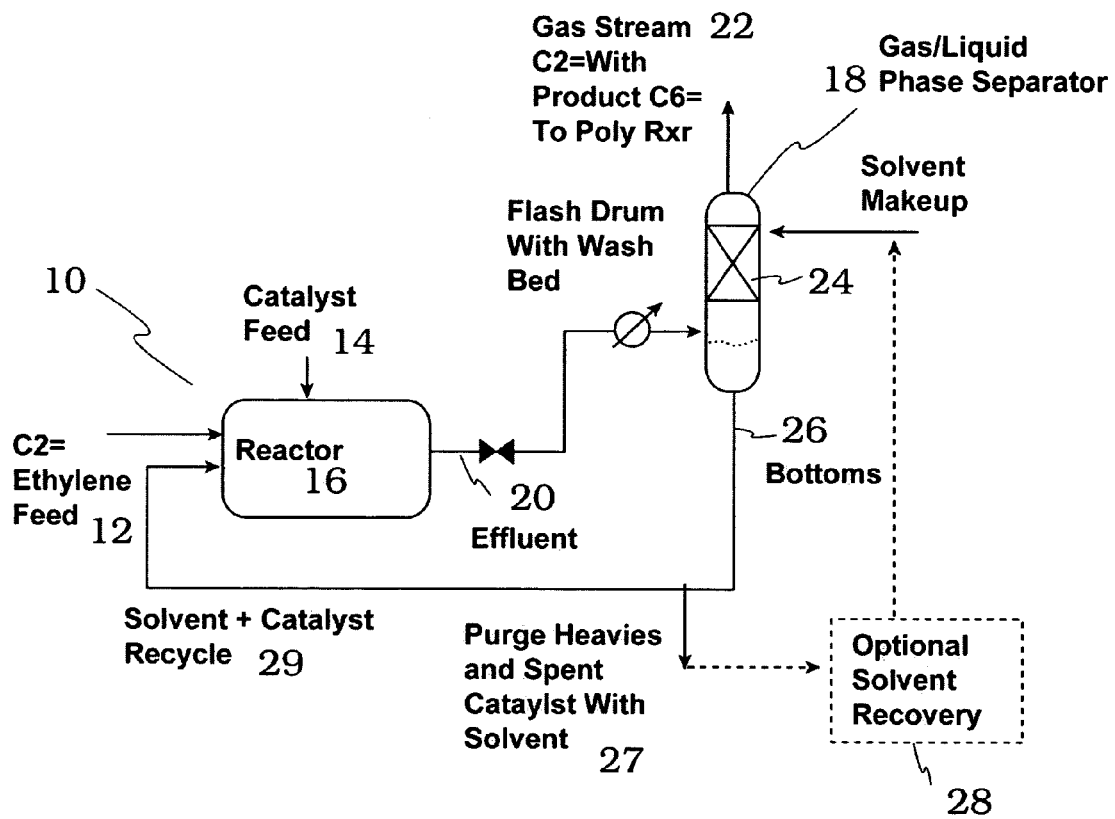
FIG. 1 depicts an illustrative schematic of the in-line process for comonomer generation utilizing a comonomer synthesis reactor and a downstream gas/liquid phase separator.

For the purposes of this invention and the claims thereto when an oligomeric material (such as a dimer, trimer, or tetramer) is referred to as comprising an olefin, the olefin present in the material is the reacted form of the olefin. Likewise, the active species in a catalytic cycle may comprise the neutral or ionic forms of the catalyst. In addition, a reactor is any container(s) in which a chemical reaction occurs.

As used herein, the new numbering scheme for the Periodic Table Groups is used as set out in CHEMICAL AND ENGINEERING NEWS, 63(5), 27 (1985). For purposes of this invention, a catalyst system is defined to be the combination of an activator and a metal ligand complex or the combination of an activator, a ligand and a metal precursor. A metal ligand complex is defined to be the product of the combination of a metal precursor and a ligand.

The phrase "optionally substituted" means that a moiety (such as a hydrocarbyl) may or may not be substituted. The term "substituted" means that at least one hydrogen atom bound to a carbon atom is replaced with a heteroatom containing group or a hydrocarbyl group. Further when the term "substituted" or "optionally substituted" introduces a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

The term "hydrocarbyl" as used herein refers to hydrocarbyl radicals containing 1 to 50 carbon atoms. Preferred hydrocarbyls contain 1 to 24 carbon atoms, more specifically 1 to 16 carbon atoms, including branched or unbranched, cyclic or acyclic, saturated or unsaturated species, such as alkyl groups, alkenyl groups, aryl groups, and the like.

Throughout this specification, the presence of one solid line and one dashed line between any pair of atoms is intended to indicate that the bond in question may be a single bond or a double bond, or a bond with bond order intermediate between single and double, such as the delocalized bonding in an aromatic ring.

Certain abbreviations used herein are as follows: "i-Pr" to refer to isopropyl; "t-Bu" to refer to tertiary-butyl; "i-Bu" to refer to isobutyl; "Me" to refer to methyl; "Et" to refer to ethyl; "Ph" to refer to phenyl; "Mes" to refer to mesityl (2,4,6-trimethyl phenyl); "TFA" to refer to trifluoroacetate; "THF" to refer to tetrahydrofuran; "TMA" to refer to $AlMe_3$; "TIBA" to refer to $Al(i-Bu)_3$, and "acac" to refer to acetylacetonate.

The present invention relates to an improved in-line process for generating linear alpha olefin comonomers (e.g. 1-butene, 1-hexene, 1-octene) from ethylene monomer using specific catalysts and/or catalyst systems as described below.

The present invention further relates to an improved reaction and separation process for generating comonomer (e.g. 1-hexene) from monomer (e.g. ethylene) using the specific catalysts and/or catalyst systems described below. In one exemplary embodiment of the present invention, the improved process may be implemented immediately before the polymerization reactor with no isolation or storage of the hexene produced. Hexene is swept out of the reaction zone or loop along with unconverted ethylene, leaving behind catalyst and heavy solvent or diluent. Specific hardware implementations of this concept include a "bubbling pot" and a reactor/knockout pot pumparound.

In an alternative embodiment of the present invention, 1-octene is produced from ethylene. The improved process of the instant invention is also adaptable to catalysts which produce both hexene and octene.

FIG. 1 depicts one exemplary process schematic of the improved in-line reaction and separation process 10 of the instant invention. In this configuration, ethylene feed 12 and catalyst feed 14 are fed to a comonomer synthesis reactor 16 (also referred to as an oligomerization reactor). The comonomer synthesis reactor 16 may be of various types, including, but not limited to a stirred tank reactor, more than one agitated vessel in series, and a long, thin tube-like contactor. If the catalyst is in the form of a fixed bed rather than slurry or solution, it may be contained in a contactor type of reactor.

This invention further relates to processes for selectively oligomerizing (e.g., trimerizing and/or tetramerizing) $C_2$ to $C_{12}$ olefins, specifically ethylene, comprising reacting a catalytic composition or compound(s), optionally with one or more activators, with the olefin in the process described herein. As referred to herein, selective oligomerization refers to producing the desired oligomer with a selectivity of the reaction being at least 70%, more specifically at least 80% by mole of oligomer, with the possibility that an acceptable amount of polymer is present, but with the preference that no polymer is present in the product. In other embodiments, less than 20 weight % of polymer is present, specifically less than 5 weight %, more specifically less than 2 weight %, based upon the total weight of monomer converted to oligomers and polymers, where a polymer is defined to mean a molecule comprising more than 100 mers. In other embodiments, selective oligomerization refers to producing two desired oligomers, with the selectivity of the two desired oligomers summing to at least 80% by sum of mole of oligomers.

In another embodiment, this invention further relates to a method to trimerize or tetramerize a $C_2$ to $C_{12}$ olefin in the processes described herein wherein the method produces at least 70% selectivity for the desired oligomer(s) (specifically at least 80%, specifically at least 85%, specifically at least 90%, specifically at least 95%, specifically at least 98%, specifically at least 99%, specifically 100%), calculated based upon the amount of the desired oligomer produced relative to the total yield; and at least 70% of the olefin monomer reacts to form product (specifically at least 80%, specifically at least 85%, specifically at least 90%, specifically at least 95%, specifically at least 98%, specifically at least 99%, specifically 100%).

In another embodiment, this invention relates to a process to trimerize or tetramerize a $C_2$ to $C_{12}$ olefin (preferably ethylene) wherein the process produces at least 70% selectivity for the desired oligomer(s) (specifically at least 80%, specifically at least 85%, specifically at least 90%, specifically at least 95%, specifically at least 98%, specifically at least 99%, specifically 100%), calculated based upon the amount of the desired oligomer produced relative to the total yield; and at least 70% of the olefin monomer reacts to form product (specifically at least 80%, specifically at least 85%, specifically at least 90%, specifically at least 95%, specifically at least 98%, specifically at least 99%, specifically 100%).

A particularly useful catalyst system for selective oligomerization in the process described herein is formed from the combination of:

1) a ligand characterized by the following general formula:

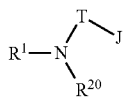

wherein:

$R^1$ and $R^{20}$ are each independently selected from the group consisting of consisting of hydrogen and optionally substituted hydrocarbyl, heteroatom containing hydrocarbyl and silyl (alternately $R^1$ and $R^{20}$ are each independently selected from the group consisting of: hydrogen and optionally substituted alkyl, heteroalkyl, cycloalkyl, heterocycloalkyl, aryl, heteroaryl, silyl and combinations thereof), provided that $R^1$ or $R^{20}$ do not equal T-J (alternately $R^1$ and $R^{20}$ are each independently a ring having from 4 to 8 atoms in the ring selected from the group consisting of substituted cycloalkyl, heterocycloalkyl, aryl and heteroaryl);

T is a bridging group, preferably represented by the formula -(T'$R^2R^3$)—, where T' is carbon or silicon, $R^2$ and $R^3$ are each independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, provided that two or more $R^2$ and/or $R^3$ groups may be joined together to form one or more optionally substituted ring systems having from 3 to 50 non-hydrogen atoms (for example, T is cyclopropyl, where T'=C, and $R^2$ and $R^3$ together form —$CH_2$—$CH_2$—; or T is cyclohexyl, where T'=C and the two $R^2$ groups together form —$CH_2$—$CH_2$—$CH_2$—$CH_2$—);

J is an optionally substituted six-membered heterocycle, containing at least one nitrogen atom as part of the ring, or J is an optionally substituted five-membered heterocycle, containing at least one nitrogen atom as part of the ring;

2) a metal precursor compound characterized by the general formula $Cr(L)_n$ where each L is independently selected from the group consisting of halide, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, wherein two or more L groups may be combined in a ring structure having from 3 to 50 non-hydrogen atoms; and n is 1, 2, 3, 4, 5, or 6; and 3) optionally, one or more activators.

In one embodiment, the ligand, as shown above, can be characterized by the following general formula, where J is a pyridyl or substituted pyridyl group:

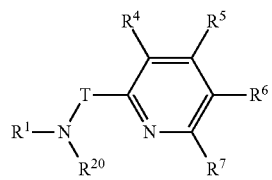

where $R^1$, $R^{20}$, and T are as described above; and $R^4$, $R^5$, $R^6$ and $R^7$ are independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, and optionally two or more $R^1$, $R^{20}$, $R^2$, $R^3$, $R^4$, $R^5$, $R^6$ and $R^7$ groups may be joined to form one or more optionally substituted ring systems.

In another embodiment, the ligand can be characterized by the following general formula:

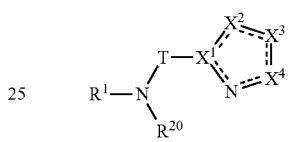

where $R^1$, $R^{20}$, and T are as described above; and $X^1$ is nitrogen or —$C(R^8)_{n''}$—, $X^2$, $X^3$, and $X^4$ are selected from the group consisting of oxygen, sulfur, —$C(R^8)_{n'}$—, —$N(R^8)_{n''}$—, and provided that at least one of $X^1$, $X^2$, $X^3$, or $X^4$ is carbon or —$C(R^8)_{n''}$—; each n' can be 1 or 2 and each n'' can be 0 or 1; and, each $R^8$ can be independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, and optionally two or more $R^1$, $R^{20}$, $R^2$, $R^3$, and $R^8$ groups may be joined to form one or more optionally substituted ring systems.

In one embodiment, $R^1$ and $R^{20}$ are each independently selected from the group consisting of hydrogen and optionally substituted alkyl, heteroalkyl, aryl, heteroaryl, silyl and combinations thereof. In another embodiment, $R^1$ and $R^{20}$ are each independently a ring having from 4 to 8 atoms in the ring generally selected from the group consisting of substituted cycloalkyl, heterocycloalkyl, aryl, and heteroaryl.

In another embodiment (including all those described above), $R^{20}$ is hydrogen and $R^1$ is selected from the group consisting of alkyl, substituted alkyl, aryl, and substituted aryl.

In still another embodiment (including all those described above), $R^1$ and $R^{20}$ can each be independently selected from hydrogen and optionally substituted alkyl groups.

In yet another embodiment (including all those described above), $R^1$ and $R^{20}$ are joined in a ring structure having from 3 to 50 non-hydrogen atoms.

In another embodiment (including all those described above), $R^1$ is not hydrogen when $R^{20}$ is a cyclic group.

In still another embodiment (including all those described above), $R^{20}$ is not a hydrogen when $R^1$ is a cyclic group.

In another embodiment (including all those described above), $R^7$ is selected from the group consisting of optionally substituted aryl and heteroaryl.

In another embodiment (including all those described above), $R^2$ is hydrogen, and $R^3$ is selected from the group consisting of aryl, substituted aryl, heteroaryl, substituted heteroaryl, alkyl and substituted alkyl groups, and —PY$_2$ where Y is selected from the group consisting of aryl, substituted aryl, heteroaryl, and substituted heteroaryl.

In some embodiments (including all those described above), $R^1$ is hydrogen and $R^{20}$ is selected from the group consisting of methyl, ethyl, propyl, butyl, pentyl, hexyl, octyl, decyl, docecyl, benzyl, and —CH$_2$CH$_2$Ph groups.

In some embodiments (including all those described above), $R^1$ and $R^{20}$ are each independently selected from the group consisting of methyl, ethyl, propyl, butyl, pentyl, hexyl, octyl, decyl, docecyl, benzyl and —CH$_2$CH$_2$Ph groups.

In some embodiments (including all those described above), $R^5$ is selected from the group consisting of —CF$_3$, H, F, Cl, —N(Me)$_2$ and —OR, wherein R is an optionally substituted alkyl group, an optionally substituted benzyl group or an optionally substituted aryl group.

In some embodiments (including all those described above), $R^3$ is selected from the group consisting of hydrogen and optionally substituted alkyl, heteroalkyl, cycloalkyl, heterocycloalkyl, silyl and combinations thereof.

The heterocycle-amine ligands, such as, pyridyl-amine ligands, described herein can be prepared according to the procedures known to those of ordinary skill in the art, for example, as described in U.S. Pat. Nos. 6,750,345, 6,713,577, and as described in US patent applications USSN (2005B030A and 2005B030B), which are incorporated by reference herein.

Preferred ligands for use herein include pyridyl-amine ligands A1-A75 as seen in the attached figures, especially ligands A4, A5, A23, A28, A29, A30, and A38.

Preferred ligands useful herein also include those represented by the following formulae:

B1

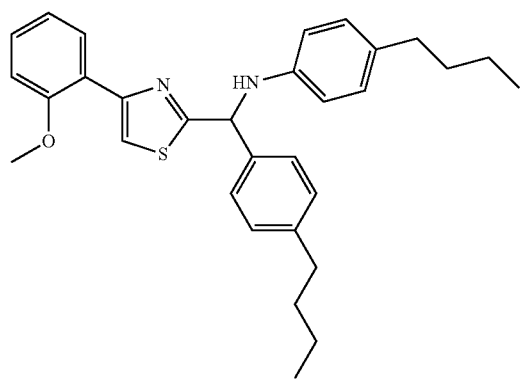

B2

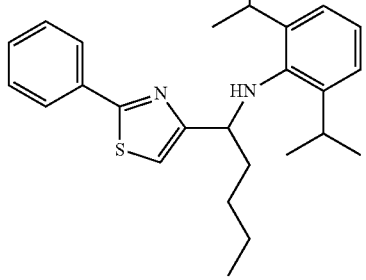

B3

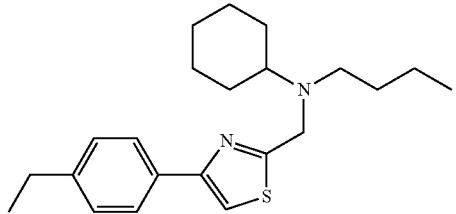

C1

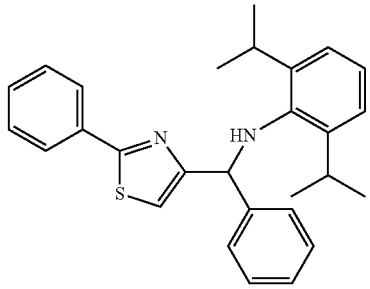

C2

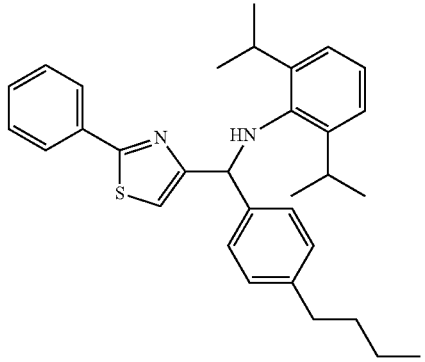

C3

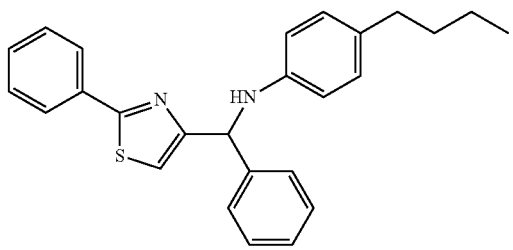

C4

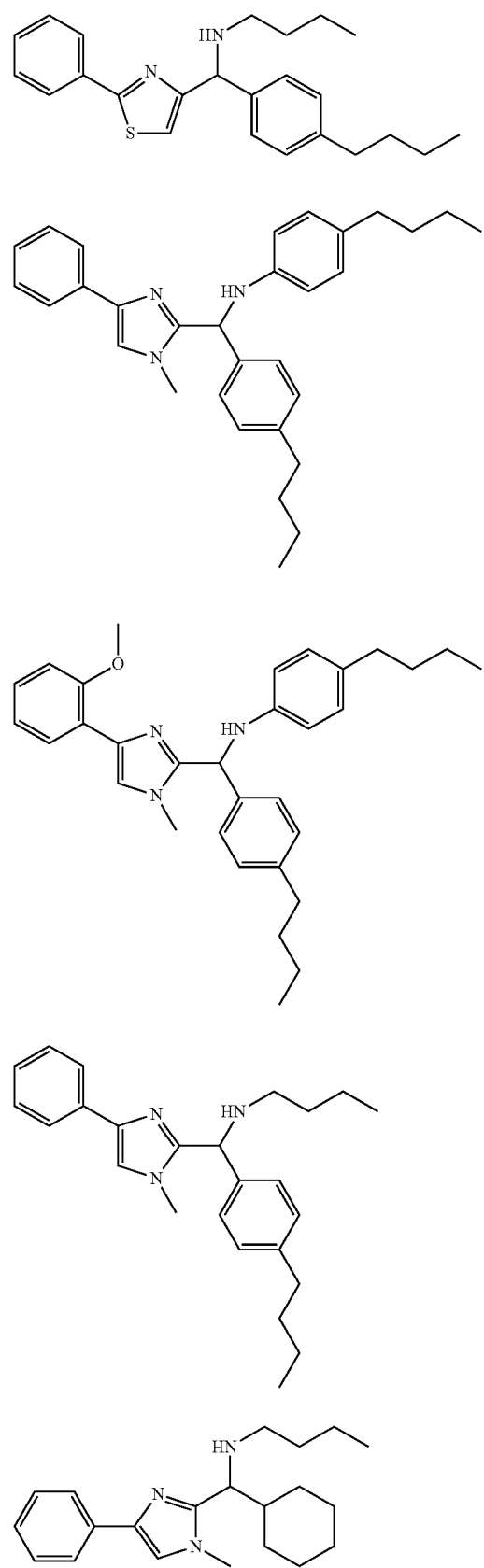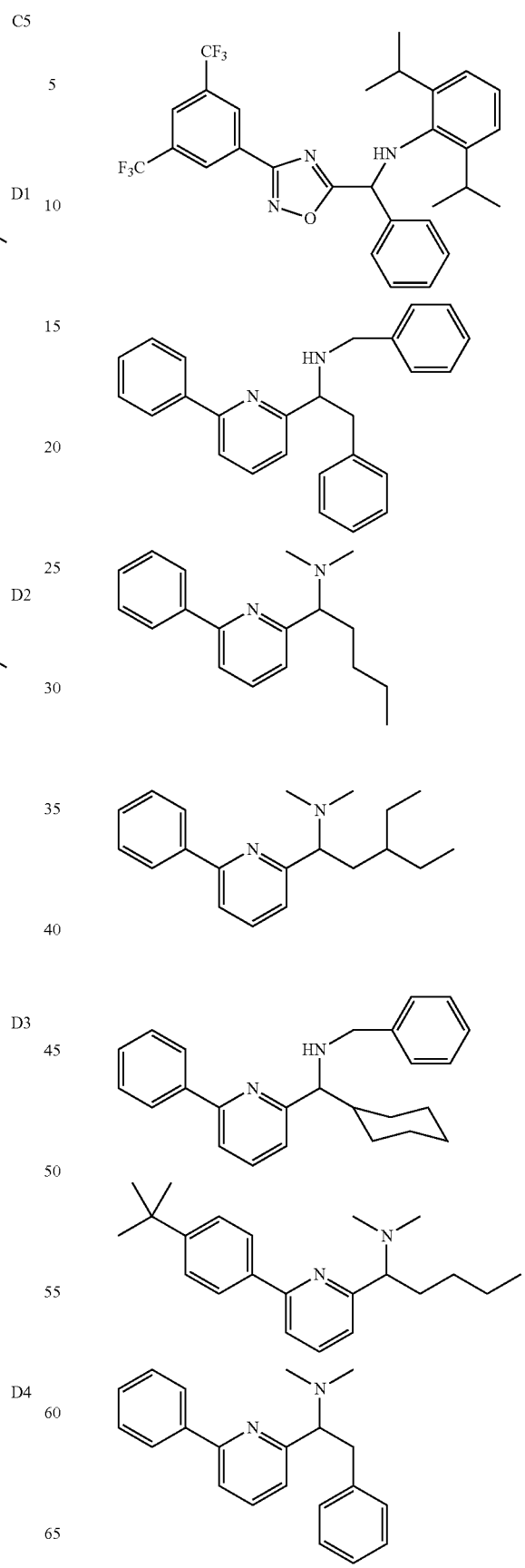

-continued

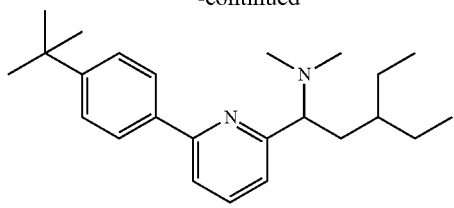

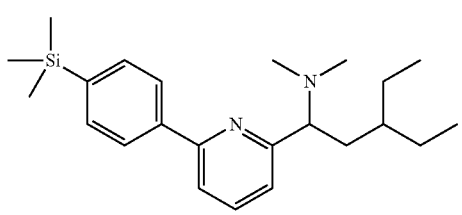

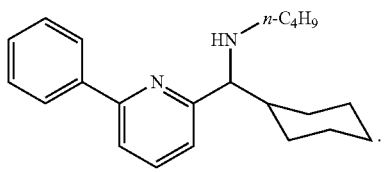

Particularly useful trimerization ligands useful herein include:

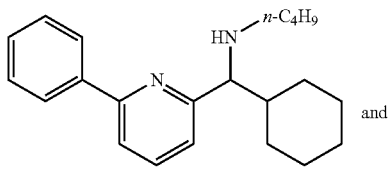 A29

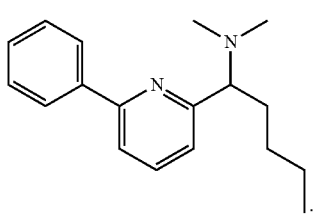 A53

Another useful catalyst and or catalyst system for oligomerization of olefins (preferably the trimerization or tetramerization of C2 to C12 olefins, such as ethylene) useful herein is formed from the combination of:

1) at least one ligand represented by the formula:

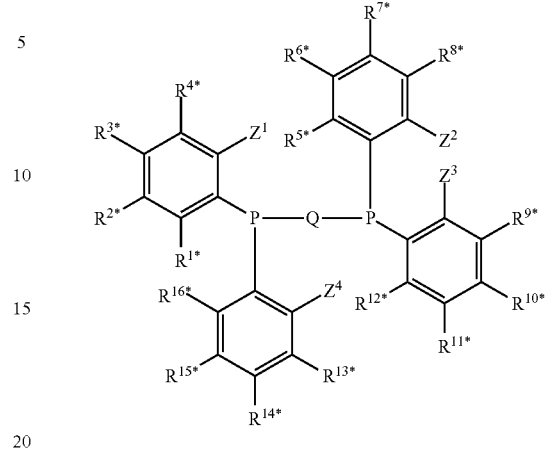

or wherein
P is phosphorus;
each of $R^{1*}$, $R^{2*}$, $R^{3*}$, $R^{4*}$, $R^{5*}$, $R^{6*}$, $R^{7*}$, $R^{8*}$, $R^{9*}$, $R^{10*}$, $R^{11*}$, $R^{12*}$, $R^{13*}$, $R^{14*}$, $R^{15*}$, and $R^{16*}$ is, independently, selected from the group consisting of hydrogen, halogen, optionally substituted hydrocarbyl and optionally substituted heteroatom containing hydrocarbyl;
each of $Z^1$, $Z^2$, $Z^3$ or $Z^4$ is, independently, selected from a first group consisting of hydrogen, a hydrocarbyl, alkoxy, aryloxy, alkylthio, arylthio, hydroxyl, mercapto and amino, (preferably at least two and less than all four of $Z^1$, $Z^2$, $Z^3$ or $Z^4$ is selected from a second group consisting of alkoxy, aryloxy, alkylthio, arylthio, hydroxyl, mercapto and amino; in alternate embodiments, $Z^1$, $Z^2$, $Z^3$ and $Z^4$ may not all be methoxy; in still further embodiments, either of the pairs of $Z^1$ and $Z^2$ or $Z^3$ and $Z^4$ are not both selected from the second group);
Q is a bridging group selected from the group consisting of optionally substituted hydrocarbyl having from 2 to 20 carbon atoms;
2) a metal precursor characterized by the general formula $Cr(L)_n$ where each L is independently selected from the group consisting of halide, alkyl, substituted alkyl, cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, and wherein two or more L groups may be combined in a ring structure having from 3 to 50 non-hydrogen atoms; n is 1, 2, 3, 4, 5, or 6; and
3) optionally, one or more activators.

In alternate embodiments, Q can be a hydrocarbyl bridge formed by an aryl or cycloalkyl group. For example, such aryl or cycloalkyl bridging groups include phenyl, naphthyl, biphenyl and cyclohexyl. In certain embodiments, the phosphorus atoms are connected apart from each other by two, three, four, five or six carbon bonds. For example, when a phenyl or cyclohexyl group is Q, the phosphorus atoms can be attached 1,2 or 1,3 or 1,4 relative to each other (ortho, meta or para).

In some embodiments, when $Z^1$, $Z^2$, $Z^3$ or $Z^4$ are each methoxy and Q is an ethylene or methylene bridge, the metal precursor is not $CrCl_3(THF)_3$;

In another alternate embodiment, three of $Z^1$, $Z^2$, $Z^3$ or $Z^4$ are, independently, selected from the group consisting alkoxy, aryloxy, alkylthio, arylthio, hydroxyl, mercapto and amino and one of $Z^1$, $Z^2$, $Z^3$ or $Z^4$ is, independently, selected from the group consisting of hydrogen and hydrocarbyl.

In another alternate embodiment, each of $Z^1$, $Z^2$, $Z^3$ or $Z^4$ is, independently, selected from the group consisting alkoxy, aryloxy, alkylthio, arylthio, hydroxyl, mercapto and amino further provided that $Z^1$, $Z^2$, $Z^3$ and $Z^4$ may not all be methoxy.

In some embodiments $Z^1$, $Z^2$, $Z^3$ and $Z^4$ are, independently selected from the group consisting of methoxy, ethoxy, propoxy, isopropoxy, butoxy, isobutoxy, tert-butoxy, pentoxy, phenoxy, methylthio, ethylthio, propylthio, isopropylthiio, butylthio, isobutylthio, tert-butylthio, phenylthio, dimethylamino, diethylamino, dipropylamino, diisopropylamino, dibutylamino, diisobutylamino, hydroxyl, and mercapto.

In some embodiments Q has from 2 to 16 carbon atoms, preferably Q is selected from the group consisting of ethyl, propyl, butyl, pentyl, hexyl, cyclohexyl, aryl, heptyl, tolyl, octyl, nonyl, decyl, phenyl, naphthyl, and dodecyl. In some embodiments each of $R^{1*}$, $R^{2*}$, $R^{3*}$, $R^{4*}$, $R^{5*}$, $R^{6*}$, $R^{7*}$, $R^{8*}$, $R^{9*}$, $R^{10*}$, $R^{11*}$, $R^{12*}$, $R^{13*}$, $R^{14*}$, $R^{15*}$, and $R^{16*}$ is, independently, selected from the group consisting of hydrogen, a hydrocarbyl group having 1 to 20 carbon atoms, a substituted hydrocarbyl group having 1 to 20 carbon atoms and halogen. In some embodiments each of $Z^1$, $Z^2$, $Z^3$ or $Z^4$ is, independently, hydrogen, alkoxy, aryloxy, alkylthio, arylthio, hydroxyl, mercapto, amino, with the alkyl or aryl or substituents on these groups are a $C_1$ to $C_{20}$ hydrocarbyl group, preferably the $C_1$ to $C_{20}$ hydrocarbyl group is selected from the group consisting of methyl, ethyl, propyl, butyl, pentyl, hexyl, cyclohexyl, aryl, heptyl, tolyl, octyl, nonyl, decyl, phenyl, napthyl, benzyl, tolyl, or dodecyl.

In a preferred embodiment, one, two, three or all four of $Z^1$, $Z^2$, $Z^3$ or $Z^4$ are selected from the group consisting of alkoxy, aryloxy, alkylthio, arylthio, hydroxyl, mercapto, and amino. In another preferred embodiment, one, two, three or all four of $Z^1$, $Z^2$, $Z^3$ or $Z^4$ are an alkoxy, preferably methoxy.

A specific group of ligands useful in this invention include those represented by the formulae:

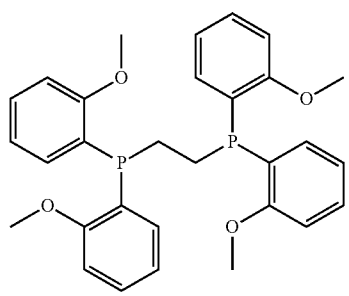

A1

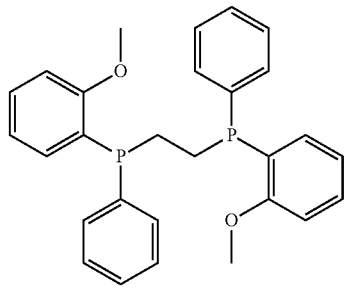

A2

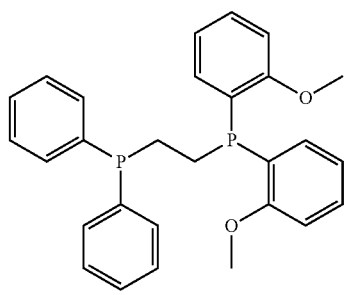

A3

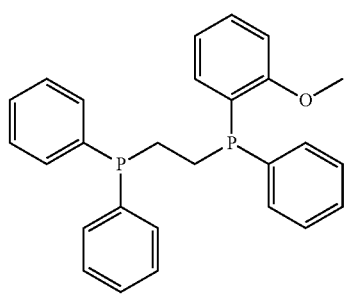

A4

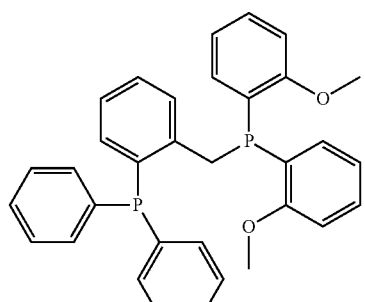

A5

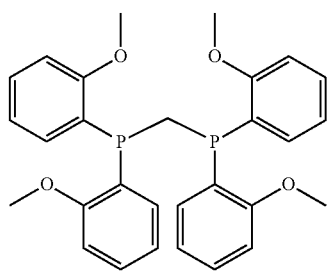

A6

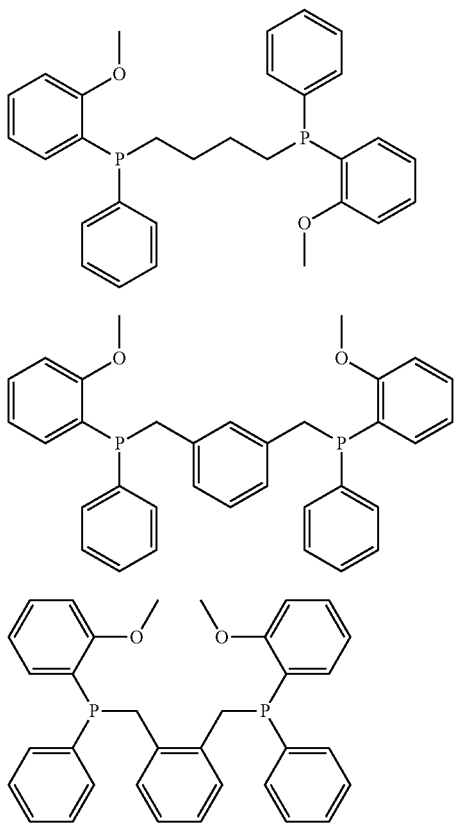

A7

A8

A9

A particularly preferred ligand is $Ar_2PCH_2CH_2P(2-MeOPh)_2$, wherein Ar is arene, Me is methyl, Ph is phenyl. Another preferred ligand is (ortho-methoxyphenyl)$_2$P—CH$_2$—CH$_2$—P(ortho-methoxyphenyl)$_2$. Another preferred ligand is (phenyl)(ortho-methoxyphenyl)P—CH$_2$—CH$_2$—P(ortho-methoxyphenyl)(phenyl) also referred to as bis[(2-methoxyphenyl)phenylphosphino]ethane. Methods to prepare such ligands are discussed in U.S. Ser. No. 60/841,226, filed Aug. 30, 2006 assigned to ExxonMobil Chemical Patents Inc.

In certain embodiments when the catalyst precursor is CrCl$_3$(THF)$_3$, the ligand is not A1 or A6. Alternately in some embodiments, when the catalyst precursor is CrCl$_3$(THF)$_3$, the ligand is A1 or A6, then the activator is modified methylalumoxane ("MMAO") and or methylalumoxane ("MAO").

More specific ligands useful in the invention include: $Ar_2PCH_2CH_2P(2-MeOPh)_2$, where Ar is arene (in particular Ar is Ph, 2-MePh, 2,6-Me2Ph, 2,4,6-Me3Ph, 1-Naphthyl, or 2-Naphthyl), Me is methyl, Ph is phenyl.

Where asymmetric substitution at the phosphine leads a chiral center, pure enantiomers, pure diastereomers, or mixtures thereof may be used.

Metal Precursor

Once the desired ligand is formed, it can be combined with a Cr atom, ion, compound or other Cr precursor compound, and in some embodiments the present invention encompasses compositions that include any of the above-mentioned ligands in combination with an appropriate Cr precursor and an optional activator.

Particularly useful Cr metal precursor compounds are represented by the formula $Cr(L)_n$ where L is an organic group, an inorganic group, or an anionic atom; and n is an integer of 1 to 6, and when n is not less than 2, L may be the same or different from each other. Each L is a ligand independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulfate, and combinations thereof. Optionally, two or more L groups are joined into a ring structure. One or more of the ligands L may be ionically bonded to Cr and, for example, L may be a non-coordinated or loosely coordinated or weakly coordinated anion (e.g., L may be selected from the group consisting of those anions described below in the conjunction with the activators). See Marks et al., Chem. Rev. 100, pp 1391-1434 (2000) for a detailed discussion of these weak interactions. The chromium precursors may be monomeric, dimeric or higher orders thereof.

In a preferred embodiment, each L is independently a hydrocarbyl, halide, alkoxy, carboxylate, diaonate, amino, ether, or amine. In an alternate embodiment, each L is independently chloride, mesityl, tetrahydrofuran, methyl, ethyl, butyl, pentyl, hexyl, octyl, phenyl, Et$_2$O, NH$_3$, NMe$_3$, acetylacetonate, 2-ethylhexanoate, neopentyl, SMe$_2$, CH$_2$—C$_6$H$_4$-o-NMe$_2$, trifluoroacetate, CH(SiMe$_3$)$_2$, p-tolyl, diisopropylamide, picolinate, or NO$_3$, where Et is ethyl, Me is methyl.

Specific examples of suitable chromium precursors include, but are not limited to (THF)$_3$CrMeCl$_2$, (Mes)$_3$Cr(THF), [{TFA}$_2$Cr(OEt$_2$)]$_2$, (THF)$_3$CrPh$_3$, CrCl$_3$(THF)$_3$, CrCl$_4$(NH$_3$)$_2$, Cr(NMe$_3$)$_2$Cl$_3$, CrCl$_3$, Cr(acac)$_3$, Cr(2-ethylhexanoate)$_3$, Cr(neopentyl)$_4$, Cr(CH$_2$—C$_6$H$_4$-o-NMe$_2$)$_3$, Cr(TFA)$_3$, Cr(CH(SiMe$_3$)$_2$)$_3$, Cr(Mes)$_2$(THF)$_3$, Cr(Mes)$_2$(THF), Cr(Mes)Cl(THF)$_2$, Cr(Mes)Cl(THF)$_{0.5}$, Cr(p-tolyl)Cl$_2$(THF)$_3$, Cr(diisopropylamide)$_3$, Cr(picolinate)$_3$, [Cr$_2$Me$_8$][Li(THF)]$_4$, CrCl$_2$(THF), Cr(NO$_3$)$_3$, [CrMe$_6$][Li(Et$_2$O)]$_3$ [CrPh$_6$][Li(THF)]$_3$, [CrPh$_6$][Li(n-Bu$_2$O)]$_3$, [Cr(C$_4$H$_8$)$_3$][Li(THF)]$_3$, and other well known chromium compounds commonly used as precursors in the formation of Cr complexes and catalysts.

Preferred metal precursors used herein can be selected from the group consisting of (THF)$_3$CrMeCl$_2$, (THF)$_3$CrCl$_3$, (Mes)$_3$Cr(THF), [{TFA}$_2$Cr(OEt$_2$)]$_2$, (THF)$_3$CrPh$_3$, and mixtures thereof.

The ligand may be mixed with a metal precursor compound prior to or simultaneously with allowing the mixture to be contacted with the reactants (e.g., monomers). The ligand to metal precursor compound ratio can be in the range of about 0.01:1 to about 100:1, more specifically in the range of about 0.1:1 to about 10:1.

Cr-ligand complexes can take a number of different coordination modes. General examples of possible coordination modes include those characterized by the following general formulas:

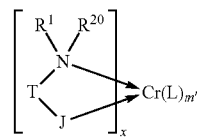

VI(a)

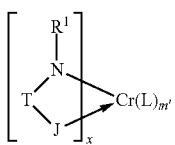
VI(b)

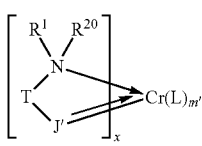
VI(c)

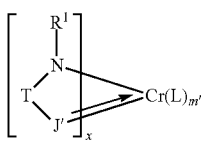
VI(d)

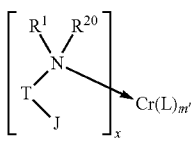
VI(e)

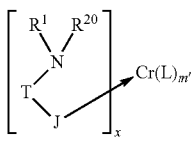
VI(f)

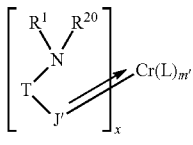
VI(g)

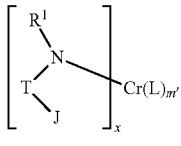
VI(h)

wherein $R^1$, $R^{20}$, L, J and T are described above; x is 1 or 2; and m' is 1, 2, 3, 4, or 5. J' is defined the same as J is defined above, provided that J' includes 2 atoms bonded to the Cr, one of which is in the ring position adjacent to the atom bonded to T, which is bonded to Cr through a dative bond, and the other of which is bonded to the Cr through a covalent bond. Numerous other coordination modes are possible, for example the ligands may bind to two chromium metal centers in a bridging fashion (see for example Cotton and Walton, *Multiple Bonds Between Metal Atoms* 1993, Oxford University Press).

In some embodiments, the ligand will be mixed with a suitable metal precursor prior to or simultaneous with allowing the mixture to be contacted to the reactants. When the ligand is mixed with the metal precursor, a metal-ligand complex is formed. In connection with the metal-ligand complex and depending on the ligand or ligands chosen, the metal-ligand complex may take the form of dimers, trimers or higher orders thereof or there may be two or more metal atoms that are bridged by one or more ligands. Furthermore, two or more ligands may coordinate with a single metal atom. The exact nature of the metal-ligand complex(es) formed depends on the chemistry of the ligand and the method of combining the metal precursor and ligand, such that a distribution of metal-ligand complexes may form with the number of ligands bound to the metal being greater than, equal to or less than the number of equivalents of ligands added relative to an equivalent of metal precursor.

In one embodiment, the metal complex is represented by the formula:

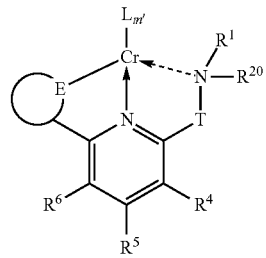

wherein $R^1$, $R^4$, $R^5$, $R^6$, $R^{20}$, T, L and m' are as described above; and E is a carbon atom that is part of an optionally substituted aryl or heteroaryl ring. In one aspect, the aryl or heteroaryl ring may be polycyclic.

Listed below are some examples of Cr-Ligand complex embodiments useful herein:

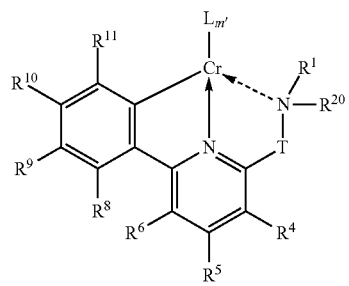

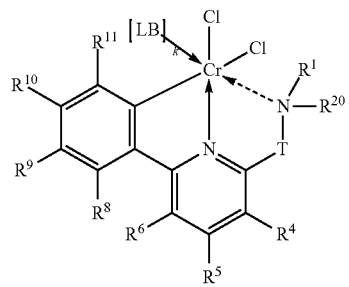

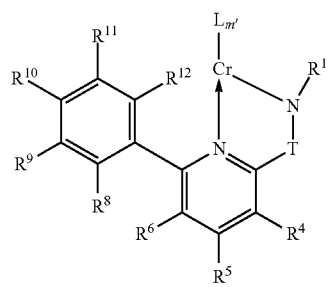

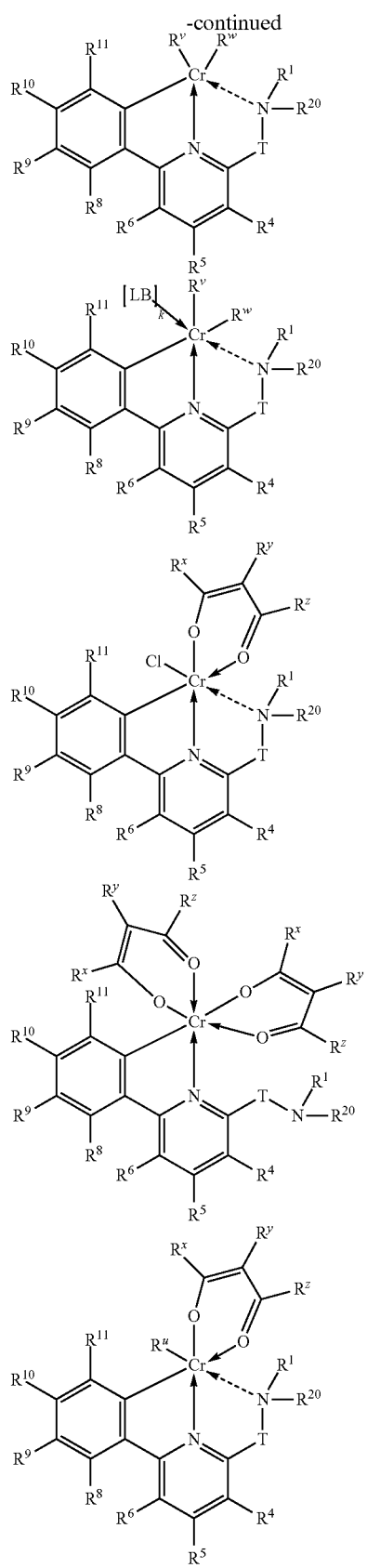

optionally substituted alkyl, heteroalkyl, aryl, heteroaryl, alkoxy, aryloxy, silyl, boryl, phosphino, amino, alkylthio, arylthio, and combinations thereof, and optionally two or more $R^8$ $R^9$, $R^{10}$, $R^{11}$ and $R^{12}$ groups may be joined to form one or more optionally substituted ring systems;

$R^u$, $R^v$, $R^w$, $R^x$, $R^y$ and $R^z$ are optionally substituted alkyl, heteroalkyl, aryl, heteroaryl;

L and m' are as defined above;

a dashed arrow indicates that the dative bond is an optional bond which may or may not be present; and LB is a Lewis base and k=0 or 1.

Some specific embodiments of Cr-Ligand complexes useful herein are shown below:

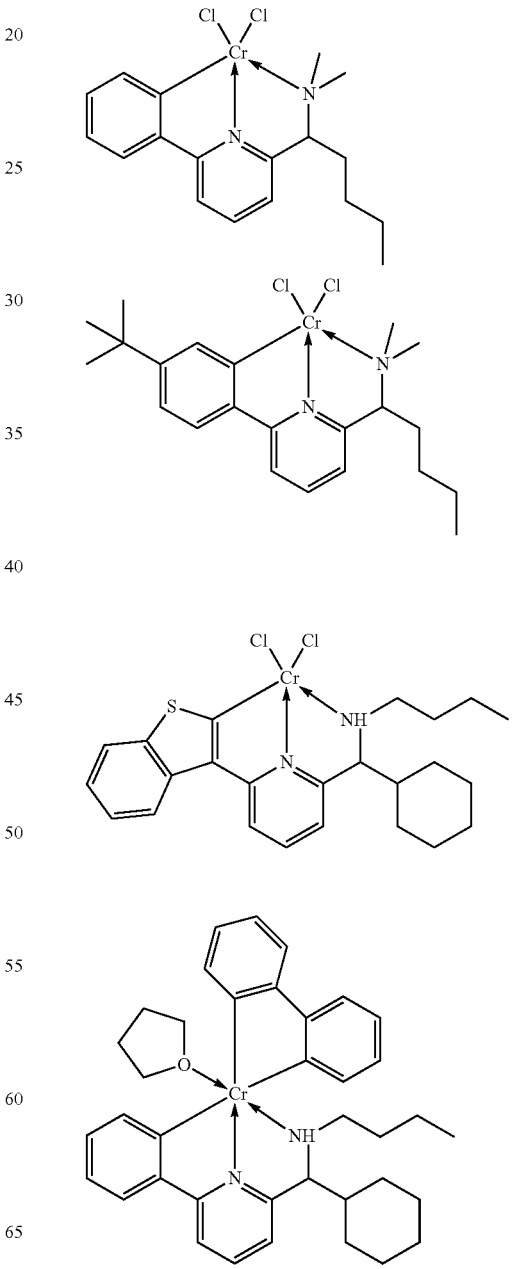

wherein $R^1$, $R^2$, $R^3$, $R^4$, $R^5$, $R^6$, $R^{20}$, T are as defined above; $R^8$ $R^9$, $R^{10}$, $R^{11}$, and $R^{12}$ are independently selected from the group consisting of hydrogen, halogen, nitro, and 25
-continued
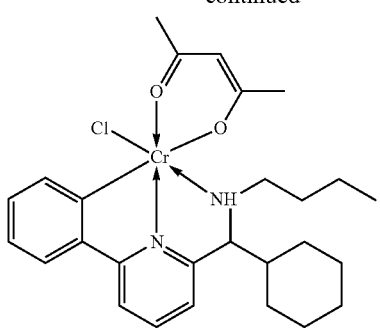
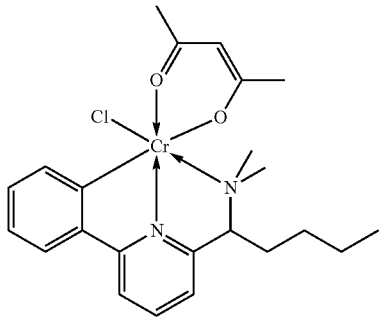
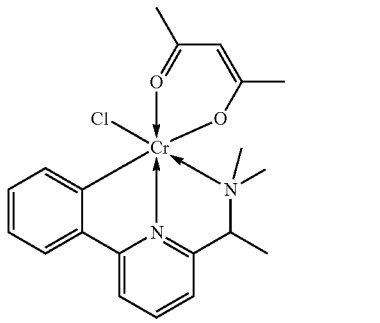
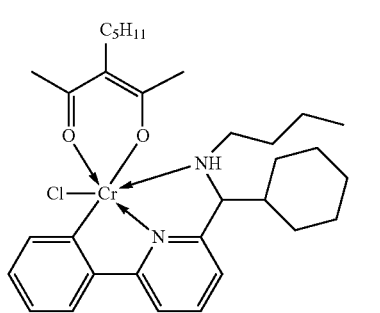
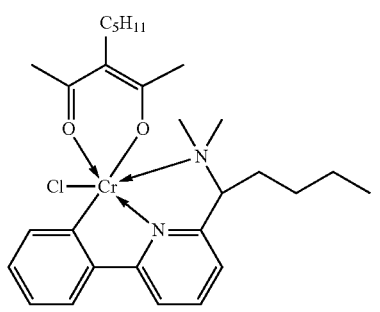
26
-continued
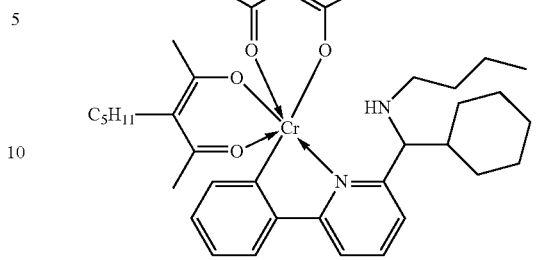
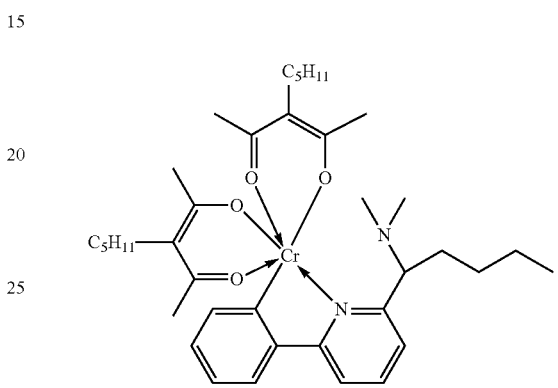
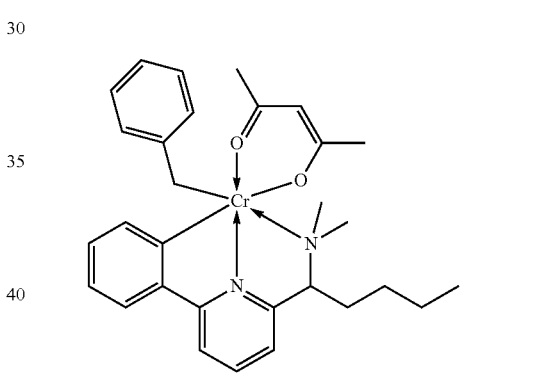
In still further embodiments, Cr-ligand complexes can take a number of different coordination modes. General examples of possible coordination modes include those represented by the formulae:
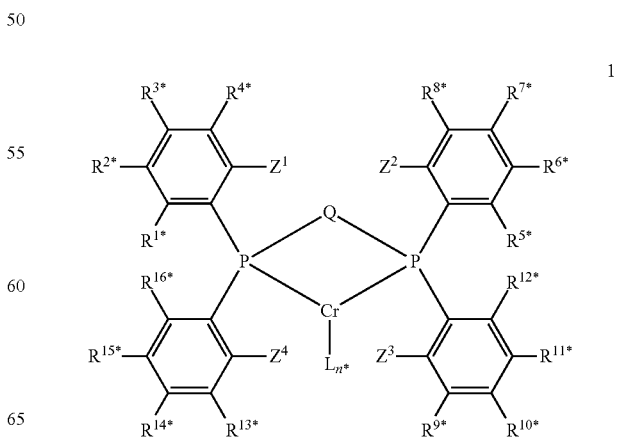

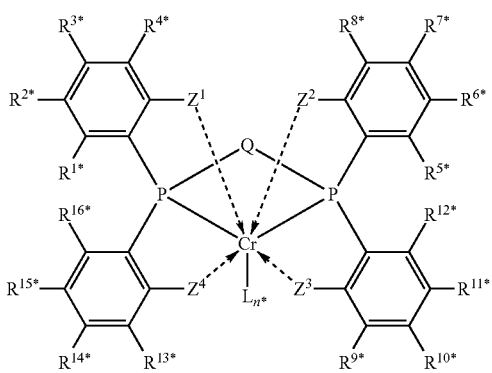

wherein n*=0, 1, 2, 3, or 4, and $R^{1*}$ to $R^{16*}$, Q, L, and $Z^1$ to $Z^4$ are as defined above. In a preferred embodiment of formula 2, any one or more of $Z^1$, $Z^2$, $Z^3$ and $Z^4$ may form a dative bond to the chromium. In certain circumstances, for instance, during catalysis, the formation of the dative bonds may be reversible. Further specific examples of Cr-ligand complexes useful in the invention are shown below:

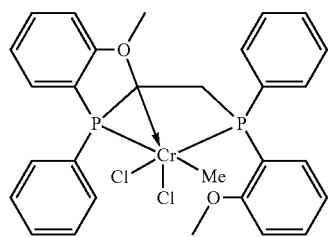

M1

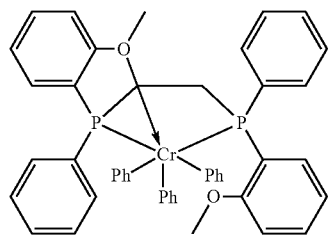

M2

Further description of such complexes and how to prepare them is disclosed in U.S. Ser. No. 60/841,226, filed Aug. 30, 2006 assigned to ExxonMobil Chemical Patents Inc.

Activators

The ligand-metal-precursor combinations and the metal ligand complexes, described above, are optionally activated in various ways to yield compositions active for selective oligomerization (preferably ethylene oligomerization). For the purposes of this patent specification and appended claims, the terms "cocatalyst" and "activator" are used herein interchangeably and are defined to be any compound which can activate any one of the ligands-metal-precursor-combinations and the metal ligand complexes, described above by converting the combination, complex, or composition into a catalytically active species. Non-limiting activators, for example, include alumoxanes, aluminum alkyls, other metal or main group alkyl or aryl compounds, ionizing activators, which may be neutral or ionic, Lewis acids, reducing agents, oxidizing agents, and combinations thereof.

In one embodiment, alumoxane activators are utilized as an activator in the compositions useful in the invention. Alumoxanes are generally oligomeric compounds containing —Al (R*)—O— sub-units, where R* is an alkyl group. Examples of alumoxanes include methylalumoxane (MAO), ethylalumoxane, isobutylalumoxane, and modified methylalumoxanes (MMAO), which include alkyl groups other than methyl such as ethyl, isobutyl, and n-octyl, such as MMAO-3A, PMAO-IP (referring to polymethylalumoxane, improved process, manufactured by Akzo-Nobel and meaning an MAO prepared from a non-hydrolytic process). Alkylalumoxanes and modified alkylalumoxanes are suitable as catalyst activators, particularly when the abstractable ligand of the catalyst is a halide, alkoxide or amide. Mixtures of different alumoxanes and modified alumoxanes may also be used. For further descriptions on production and use of alumoxanes, see U.S. Pat. Nos. 4,665,208, 4,952,540, 5,041,584, 5,091,352, 5,206, 199, 5,204,419, 4,874,734, 4,924,018, 4,908,463, 4,968,827, 5,329,032, 5,248,801, 5,235,081, 5,157,137, 5,103,031 and EP0561476A1, EP0279586B1, EP0516476A1, EP0594218A1 and WO94/10180.

When the activator is an alumoxane (modified or unmodified), some embodiments select the maximum amount of activator at a 5000-fold molar excess Al/Cr over the catalyst precursor. The minimum preferred activator-to-catalyst-precursor is a 1:1 molar ratio. More specifically, the Al/Cr ratio is from 1000:1 to 100:1.

It may be preferable to use a visually clear methylalumoxane. A cloudy or gelled alumoxane can be filtered to produce a clear solution or clear alumoxane can be decanted from the cloudy solution. Another particularly useful alumoxane is a modified methyl alumoxane (MMAO) cocatalyst type 3A (commercially available from Akzo Chemicals, Inc. under the trade name Modified Methylalumoxane type 3A, covered under patent number U.S. Pat. No. 5,041,584).

Aluminum alkyl or organoaluminum compounds which may be utilized as activators (or scavengers) include trimethylaluminum, triethylaluminum, triisobutylaluminum, tri-n-hexylaluminum, tri-n-octylaluminum, diisobutylaluminum hydride, ethylaluminum dichloride, diethylaluminum chloride, diethylaluminum ethoxide and the like.

Ionizing Activators

In some embodiments, the activator includes compounds that may abstract a ligand making the metal complex cationic and providing a charge-balancing non-coordinating or weakly coordinating anion. The term "non-coordinating anion" (NCA) means an anion which either does not coordinate to said cation or which is only weakly coordinated to said cation thereby remaining sufficiently labile to be displaced by a neutral Lewis base.

It is within the scope of this invention to use an ionizing or stoichiometric activator, neutral or ionic, such as tri(n-butyl) ammonium tetrakis (pentafluorophenyl) boron, a tris(perfluorophenyl) boron metalloid precursor or a tris(perfluoronaphthyl) boron metalloid precursor, polyhalogenated heteroborane anions (WO98/43983), boric acid (U.S. Pat. No. 5,942,459) or combination thereof. It is also within the scope of this invention to use neutral or ionic activators alone or in combination with alumoxane or modified alumoxane activators.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. In some embodiments, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). In other embodiments, the three groups are alkyls having 1 to 4 carbon groups, phenyl, naphthyl or mixtures thereof. In further embodiments, the three groups are halogenated, specifically fluorinated, aryl groups. In even further embodiments, the neutral stoichiometric activator is tris(perfluorophenyl) boron or tris(perfluoronaphthyl) boron.

Ionic stoichiometric activator compounds may contain an active proton, or some other cation associated with, but not coordinated to, or only loosely coordinated to, the remaining ion of the ionizing compound. Such compounds and the like are described in European publications EP0570982A1, EP0520732A1, EP0495375A1, EP0500944B1, EP0277003A1 and EP0277004A1, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Ionic catalysts can be prepared by reacting a Cr compound with some neutral Lewis acids, such as $B(C_6F_6)_3$, which upon reaction with the abstractable ligand (X) of the Cr compound forms an anion, such as $([B(C_6F_5)_3(X)]^-)$, which stabilizes the cationic Cr species generated by the reaction. The catalysts can be prepared with activator components which are ionic compounds or compositions.

In some embodiments, compounds useful as an activator component in the preparation of the ionic catalyst systems used in the process of this invention comprise a cation, which is optionally a Brönsted acid capable of donating a proton, and a compatible non-coordinating anion which is capable of stabilizing the active catalyst species which is formed when the two compounds are combined and said anion will be sufficiently labile to be displaced by olefinic substrates or other neutral Lewis bases such as ethers, nitriles and the like. Two classes of compatible non-coordinating anions useful herein have been disclosed in EP0277003A1 and EP0277004A1 published 1988: anionic coordination complexes comprising a plurality of lipophilic radicals covalently coordinated to and shielding a central charge-bearing metal or metalloid core; and, anions comprising a plurality of boron atoms such as carboranes, metallacarboranes and boranes.

In one preferred embodiment, the stoichiometric activators include a cation and an anion component, and may be represented by the following formula:

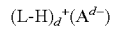

where L is a neutral Lewis base; H is hydrogen; $(L-H)^+$ is a Brönsted acid; $A^{d-}$ is a non-coordinating anion having the charge d−; and d is an integer from 1 to 3. The cation component, $(L-H)_d^+$ may include Brönsted acids such as protons or protonated Lewis bases or reducible Lewis acids capable of protonating or abstracting a moiety, such as an alkyl or aryl, from the bulky ligand chromium catalyst precursor, resulting in a cationic transition metal species.

The activating cation $(L-H)_d^+$ may be a Brönsted acid, capable of donating a proton to the transition metal catalytic precursor resulting in a transition metal cation, including ammoniums, oxoniums, phosphoniums, silyliums, and mixtures thereof, specifically ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers such as dimethyl ether diethyl ether, tetrahydrofuran and dioxane, sulfoniums from thioethers, such as diethyl thioethers and tetrahydrothiophene, and mixtures thereof. The activating cation $(L-H)_d^+$ may also be a moiety such as silver, tropylium, carbeniums, ferroceniums and mixtures, specifically carboniums and ferroceniums. In one embodiment $(L-H)_d^+$ can be triphenyl carbonium.

The anion component $A^{d-}$ includes those having the formula $[M^{k+}Q_n]^{d-}$ wherein k is an integer from 1 to 3; n is an integer from 2-6; n−k=d; M is an element selected from Group 13 of the Periodic Table of the Elements, specifically boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Specifically, each Q is a fluorinated hydrocarbyl group having 1 to 20 carbon atoms, more specifically each Q is a fluorinated aryl group, and most specifically each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of boron compounds which may be used as an activating cocatalyst herein are tri-substituted ammonium salts such as: trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium)tetraphenylborate, tropillium tetraphenylborate, triphenylcarbenium tetraphenylborate, triphenylphosphonium tetraphenylborate, triethylsilylium tetraphenylborate, benzene(diazonium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis (pentafluorophenyl)borate, tropillium tetrakis (pentafluorophenyl)borate, triphenylcarbenium tetrakis (pentafluorophenyl)borate, triphenylphosphonium tetrakis (pentafluorophenyl)borate, triethylsilylium tetrakis (pentafluorophenyl)borate, benzene(diazonium) tetrakis (pentafluorophenyl)borate, trimethylammonium tetrakis-(2,3,4,6-tetrafluorophenyl) borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl)ammonium tetrakis-(2,3,4,6-tetrafluorophenyl) borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl) borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, trimethylammonium tetrakis (perfluoronaphthyl)borate, triethylammonium tetrakis (perfluoronaphthyl)borate, tripropylammonium tetrakis (perfluoronaphthyl)borate, tri(n-butyl)ammonium tetrakis (perfluoronaphthyl)borate, tri(t-butyl)ammonium tetrakis (perfluoronaphthyl)borate, N,N-dimethylanilinium tetrakis (perfluoronaphthyl)borate, N,N-diethylanilinium tetrakis (perfluoronaphthyl)borate, N,N-dimethyl-(2,4,6-trimethylanilinium) tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis (perfluoronaphthyl)borate, trimethylammonium tetrakis (perfluorobiphenyl)borate, triethylammonium tetrakis (perfluorobiphenyl)borate, tripropylammonium tetrakis (perfluorobiphenyl)borate, tri(n-butyl)ammonium tetrakis (perfluorobiphenyl)borate, tri(t-butyl)ammonium tetrakis (perfluorobiphenyl)borate, N,N-dimethylanilinium tetrakis (perfluorobiphenyl)borate, N,N-diethylanilinium tetrakis (perfluorobiphenyl)borate, N,N-dimethyl-(2,4,6-trimethylanilinium) tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis (perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri (n-butyl)ammonium tetrakis(3,5-bis(trifluoromethyl)phenyl)borate, tri(t-butyl)ammonium tetrakis(3,5-bis (trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis (trifluoromethyl)phenyl)borate, tropillium tetrakis(3,5-bis (trifluoromethyl)phenyl)borate, triphenylcarbenium tetrakis (3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl) phenyl)borate, benzene(diazonium) tetrakis(3,5-bis(trifluoromethyl)phenyl)borate, and dialkyl ammonium salts such as: di-(i-propyl)ammonium tetrakis(pentafluorophenyl)borate, and dicyclohexylammonium tetrakis(pentafluorophenyl)borate; and additional tri-substituted phosphonium salts such as tri(o-tolyl)phosphonium tetrakis(pentafluorophenyl) borate, and tri(2,6-dimethylphenyl)phosphonium tetrakis (pentafluorophenyl)borate. Specifically useful ionic stoichiometric activators include: N,N-dimethylanilinium tetra (perfluorophenyl)borate, N,N-dimethylanilinium tetrakis (perfluoronaphthyl)borate, N,N-dimethylanilinium tetrakis (perfluorobiphenyl)borate, N,N-dimethylanilinium tetrakis (3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis (3,5-bis(trifluoromethyl)phenyl)borate, and triphenylcarbenium tetra(perfluorophenyl)borate.

Other examples of preferred ionizing activators include, $HNMe(C_{18}H_{37})_2{}^+B(C_6F_5)_4{}^-$; $HNPh(C_{18}H_{37})_2{}^+B(C_6F_5)_4{}^-$ and $((4\text{-}n\text{-}Bu\text{-}C_6H_4)NH(n\text{-}hexyl)_2)^+B(C_6F_5)_4{}^-$ and $((4\text{-}n\text{-}Bu\text{-}C_6H_4)NH(n\text{-}decyl)_2)^+B(C_6F_5)_4{}^-$. Specific preferred $(L^*\text{-}H)^+$ cations are N,N-dialkylanilinium cations, such as $HNMe_2Ph^+$, substituted N,N-dialkylanilinium cations, such as $(4\text{-}n\text{-}Bu\text{-}C_6H_4)NH(n\text{-}C_6H_{13})_2{}^+$ and $(4\text{-}n\text{-}Bu\text{-}C_6H_4)NH(n\text{-}C_{10}H_{21})_2{}^+$ and $HNMe(C_{18}H_{37})_2{}^+$. Specific examples of anions are tetrakis(3,5-bis(trifluoromethyl)phenyl)borate and tetrakis(pentafluorophenyl)borate.

In one embodiment, activation methods using ionizing ionic compounds not containing an active proton but capable of producing an active oligomerization catalyst are also contemplated. Such methods are described in relation to metallocene catalyst compounds in EP0426637A1, EP0573403A1 and U.S. Pat. No. 5,387,568, which are all herein incorporated by reference.

The process can also employ cocatalyst compounds or activator compounds that are initially neutral Lewis acids but form a cationic metal complex and a noncoordinating anion, or a zwitterionic complex upon reaction with the compounds of this invention. For example, tris(pentafluorophenyl) boron or aluminum may act to abstract a hydrocarbyl or hydride ligand to yield a cationic metal complex and stabilizing non-coordinating anion.

In some embodiments, ionizing activators may be employed as described in Köhn et al. (*J. Organomet. Chem.*, 683, pp 200-208, (2003)) to, for example, improve solubility.

In another embodiment, the aforementioned cocatalyst compounds can also react with the compounds to produce a neutral, uncharged catalyst capable of selective ethylene oligomerization. For example, Lewis acidic reagents such as, for example, alkyl or aryl aluminum or boron compounds, can abstract a Lewis basic ligand such as, for example, THF or Et$_2$O, from a compound yielding a coordinatively unsaturated catalyst capable of selective ethylene oligomerization. When the cations of noncoordinating anion precursors are Brönsted acids such as protons or protonated Lewis bases (excluding water), or reducible Lewis acids such as ferrocenium or silver cations, or alkali or alkaline earth metal cations such as those of sodium, magnesium or lithium, the activator-to-catalyst-precursor molar ratio may be any ratio, however, useful ratios can be from 1000:1 to 1:1.

Combinations of two or more activators may also be used in the practice of this invention.

Another suitable ion forming, activating cocatalyst comprises a salt of a cationic oxidizing agent and a noncoordinating, compatible anion characterized by the general formula:

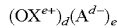

where $OX^{e+}$ is a cationic oxidizing agent having a charge of e+; e is an integer from 1 to 3; d is an integer from 1 to 3, and $A^{d-}$ is as previously defined. Examples of cationic oxidizing agents include: ferrocenium, hydrocarbyl-substituted ferrocenium, Ag$^+$, or Pb$^{+2}$. Preferred embodiments of $A^{d-}$ are those anions previously defined with respect to the Brönsted acid containing activators, especially tetrakis(pentafluorophenyl)borate.

Group 13 Reagents, Divalent Metal Reagents, and Alkali Metal Reagents

Other general activators or compounds useful in an oligomerization reaction may be used. These compounds may be activators in some contexts, but may also serve other functions in the reaction system, such as alkylating a metal center or scavenging impurities. These compounds are within the general definition of "activator," but are not considered herein to be ion-forming activators. These compounds include a group 13 reagent that may be characterized by the formula $G^{13}R^{50}{}_{3-p}D_p$ where $G^{13}$ is selected from the group consisting of B, Al, Ga, In, and combinations thereof, p is 0, 1 or 2, each $R^{50}$ is independently selected from the group consisting of hydrogen, halogen, and optionally substituted alkyl, alkenyl, alkynyl, heteroalkyl, heteroalkenyl, heteroalkynyl, aryl, heteroaryl, and combinations thereof, and each D is independently selected from the group consisting of halogen, hydrogen, alkoxy, aryloxy, amino, mercapto, alkylthio, arylthio, phosphino and combinations thereof.

In other embodiments, a divalent metal reagent may be used that is characterized by the general formula $M'R^{50}{}_{2-p'}D_{p'}$, and p' is 0 or 1 in this embodiment and $R^{50}$ and D are as defined above. M' is the metal and is selected from the group consisting of Mg, Ca, Sr, Ba, Zn, Cd, Cu and combinations thereof.

In still other embodiments, an alkali metal reagent may be used that is defined by the general formula $M^{iv}R^{50}$ and in this embodiment $R^{50}$ is as defined above, and $M^{iv}$ is the alkali metal and is selected from the group consisting of Li, Na, K, Rb, Cs and combinations thereof. Additionally, hydrogen and/or silanes may be used in the catalytic composition or added to the polymerization system. Silanes may be characterized by the formula $SiR^{50}_{4-q}D_q$ where $R^{50}$ is defined as above, q is 1, 2, 3 or 4 and D is as defined above, with the proviso that at least one D is hydrogen.

Non-limiting examples of Group 13 reagents, divalent metal reagents, and alkali metal reagents useful as activators for the catalyst compounds described above include methyl lithium, butyl lithium, phenyl lithium, dihexylmercury, butylmagnesium, diethylcadmium, benzylpotassium, diethyl zinc, tri-n-butyl aluminum, diisobutyl ethylboron, diethylcadmium, di-n-butyl zinc and tri-n-amyl boron, and, in particular, the aluminum alkyls, such as trihexyl-aluminum, triethylaluminum, trimethylaluminum, and triisobutyl aluminum, diisobutyl aluminum bromide, diethylaluminum chloride, ethylaluminum dichloride, isobutyl boron dichloride, methyl magnesium chloride, ethyl beryllium chloride, ethyl calcium bromide, diisobutyl aluminum hydride, methyl cadmium hydride, diethyl boron hydride, hexylberyllium hydride, dipropylboron hydride, octylmagnesium hydride, butyl zinc hydride, dichloroboron hydride, di-bromo-aluminum hydride and bromocadmium hydride. Other Group 13 reagents, divalent metal reagents, and alkali metal reagents useful as activators for the catalyst compounds described above are known to those in the art, and a more complete discussion of these compounds may be found in U.S. Pat. Nos. 3,221,002 and 5,093,415, which are herein fully incorporated by reference.

Other activators include those described in PCT publication WO98/07515 such as tris(2,2',2"-nonafluorobiphenyl) fluoroaluminate, which publication is fully incorporated herein by reference. Combinations of activators are also contemplated by the invention, for example, alumoxanes and ionizing activators in combinations, see for example, EP0573120B1, PCT publications WO94/07928 and WO95/14044 and U.S. Pat. Nos. 5,153,157 and 5,453,410, all of which are herein fully incorporated by reference.

Other suitable activators are disclosed in WO98/09996, incorporated herein by reference, which describes activating bulky ligand metallocene catalyst compounds with perchlorates, periodates and iodates including their hydrates. WO98/30602 and WO98/30603, incorporated by reference, describe the use of lithium (2,2'-bisphenyl-ditrimethylsilicate)•4THF as an activator for a bulky ligand metallocene catalyst compound. WO99/18135, incorporated herein by reference, describes the use of organo-boron-aluminum activators. EP0781299B1 describes using a silylium salt in combination with a non-coordinating compatible anion. Also, methods of activation such as using radiation (see EP0615981B1 herein incorporated by reference), electro-chemical oxidation, and the like are also contemplated as activating methods for the purposes of rendering the chromium complexes or compositions active for the selective oligomerization of olefins. Other activators or methods are described in for example, U.S. Pat. Nos. 5,849,852, 5,859,653 and 5,869,723 and WO98/32775, WO99/42467 (dioctadecylmethylammonium-bis(tris(pentafluorophenyl)borane) benzimidazolide), which are herein incorporated by reference.

Additional optional activators include metal salts of non-coordinating or weakly coordinating anions, for example where the metal is selected from Li, Na, K, Ag, Ti, Zn, Mg, Cs, and Ba.

It is within the scope of this invention that metal-ligand complexes and or ligand-metal-precursor-combinations can be combined with one or more activators or activation methods described above. For example, a combination of activators has been described in U.S. Pat. Nos. 5,153,157 and 5,453,410, EP0573120B1, and PCT publications WO94/07928 and WO95/14044. These documents all discuss the use of an alumoxane in combination with an ionizing activator.

Preferred activators used in the method of the present invention can be selected from the group consisting of modified methylalumoxane (MMAO), methylalumoxane (MAO), trimethylaluminum (TMA), triisobutyl aluminum (TIBA), polymethylalumoxane-IP (PMAO), N,N-di(n-decyl)-4-n-butyl-anilinium tetrakis(perfluorophenyl)borate, and mixtures thereof.

Typically, the molar ratio of metal (from the metal-ligand-complex or the ligand-metal-precursor-combination) to activator (specifically Cr:activator, specifically Cr:Al or Cr:B) can range from 1:1 to 1:5000. In another embodiment, the molar ratio of metal to activator employed can range from 1:1 to 1:500. In another embodiment, the molar ratio of metal to activator employed can range from 1:1 to 1:50. In another embodiment, the molar ratio of chromium to activator employed can range from 1:1 to 1:500. In another embodiment, the molar ratio of chromium to activator employed can range from 1:1 to 1:50.

In embodiments where more than one activator is used, the order in which the activators are combined with the metal-ligand-complex or the ligand-metal-precursor-combination may be varied.

Very generally, the oligomerization can be carried out in the Ziegler-Natta or Kaminsky-Sinn methodology, including temperatures from −100° C. to 300° C. and pressures from atmospheric to 3000 atmospheres (303,900 kPa). Suspension, solution, slurry, gas phase, or high-pressure oligomerization processes may be employed with the processes of this invention. Such processes can be run in a batch, semi-batch, or continuous mode.

Suitable solvents and or diluents for oligomerization are non-coordinating, inert liquids. Examples include mineral oil, straight and branched-chain hydrocarbons such as isobutane, butane, pentane, isopentane, hexane, isohexane, heptane, octane, dodecane, and mixtures thereof; cyclic and alicyclic hydrocarbons such as cyclohexane, cycloheptane, methylcyclohexane, methylcycloheptane, and mixtures thereof, perhalogenated hydrocarbons such as perfluorinated $C_{4-10}$ alkanes, chlorobenzene, and aromatic and alkylsubstituted aromatic compounds such as benzene, toluene, mesitylene, and xylene. Suitable solvents and or diluents also include liquid olefins which may act as monomers or comonomers including ethylene, propylene, 1-butene, 1-hexene, 1-pentene, 3-methyl-1-pentene, 4-methyl-1-pentene, 1-octene, and 1-decene. Mixtures of the foregoing are also suitable. With regard to catalyst solvent and or diluent, there is flexibility as far as what catalyst solvent/diluent may be used. Particularly preferred solvents/diluents include, but are not limited to, the comonomer product (e.g. 1-butene, 1-hexene, 1-octene), C4+ paraffins (e.g. isopentane, isobutane), cycloparaffins, and aromatics (e.g. toluene). If the catalyst is in the form of an immobilized or fixed bed, it may not require additional extraneous solvent. In another exemplary embodiment, the catalyst to the comonomer synthesis reactor may be provided in the form of an immobilized or fixed bed, hence eliminating the need for a solvent altogether.

Other additives that are useful in an oligomerization reaction may be employed, such as scavengers, promoters, modifiers, reducing agents, oxidizing agents, dihydrogen, aluminum alkyls, or silanes. For example, Jolly et al. (*Organometallics,* 16, pp 1511-1513 (1997)) has reported the use of magnesium as a reducing agent for Cr compounds that were synthesized as models for intermediates in selective ethylene oligomerization reactions.

In some useful embodiments, the activator (such as methylalumoxane or modified methylalumoxane-3A) is combined with the metal-ligand-complex or the ligand-metal-precursor-combination immediately prior to introduction into the reactor. Such mixing may be achieved by mixing in a separate tank then swift injection into the reactor, mixing in-line just prior to injection into the reactor, or the like. It has been observed that in some instances, a short activation time is very useful. Likewise in-situ activation, where the catalyst system components are injected separately into the reactor, with or without monomer, and allowed to combine within the reactor directly is also useful in the practice of this invention. In some embodiments, the catalyst system components are allowed to contact each other for 30 minutes or less, prior to contact with monomer, alternately for 5 minutes or less, alternately for 3 minutes or less, alternately for 1 minute or less.

The comonomer synthesis reactor 16 is separate from the subsequent gas/liquid phase separator 18, which allows for separate control of reaction and separation conditions. The reactor temperature and pressure are controlled to provide for acceptable reaction rates and selectivities, as well as to provide for phase separation.

With regard to catalyst solvent and or diluent, there is flexibility as far as what catalyst solvent and or diluent, if any, may be used. If a catalyst solvent and or diluent is used, it should be less volatile than hexene, and preferably less volatile than octene, such that it is not swept out along with hexene product. If decene recovery is desired and the solvent and or diluent is a hydrocarbon, then the solvent and or diluent should have volatility different than decene. On the other hand, if a solvent and or diluent is used that is compatible with the polymerization process (e.g. isobutane), it may be acceptable to allow large amounts of that solvent and or diluents to leave the oligomerization reactor 16 along with the ethylene and hexene. Examples of other suitable catalyst solvents and or diluents include C5+ paraffins (preferable branched, e.g. isopentane), cycloparaffins, and aromatics. If the catalyst is in the form of a fixed bed or a slurry, it may not require additional extraneous solvent and or diluent.

Reaction conditions are selected to give from about 5% to about 75%, preferably from about 10% to about 50% conversion of feed ethylene. Some of the chromium catalysts disclosed by Phillips, for example as disclosed in U.S. Pat. No. 5,543,375, permit a range of conditions. One exemplary, but non-limiting set of conditions, is a reaction temperature of from about 80 to about 150° C., and a reaction pressure of from about 300 to about 700 psi. However, when utilizing an ethylene feed 12, a reaction temperature of from about 60 to about 110° C. is preferred. Process conditions may be tuned to obtain desired phase separations as well as reactivity. Residence time is flexible, and is chosen to provide a desired level of ethylene conversion. A range of average reaction residence time of from about 30 minutes to about 4 hours is contemplated when using Phillips catalysts with a backmixed or pump around type of comonomer synthesis reactor 16 where most of the catalyst in the reactor 16 at a given time is not "fresh", but has been circulating around for some time before becoming deactivated. The range of reaction residence times may depend on other factors, such as the nature and amount of the catalyst.

The effluent 20 from the comonomer synthesis reactor 16 is directed to the gas/liquid phase separator 18, where the gas stream 22 exits the separator 18. A catalyst deactivator (e.g. water or alcohol) may be added to effluent 20. The gas stream 22 contains predominately ethylene along with comonomer, such as 1-hexene or 1-octene. The gas/liquid phase separator 18 may include, but is not limited to, a simple knockout vessel or other one-stage phase separator, but it may also include some trays or packing 24 in the zone where vapor is going up, with reflux liquid flowing down, to sharpen the C6/C8 or C8/C10 separation and also to wash down any catalyst or heavies that were carried upwards. In one embodiment, the ethylene is bubbled through a stirred tank or pot, and exits into a vapor space above the liquid.

In another alternative embodiment, some ethylene (not shown) is added to the separator 18 below the feed entrance point, to strip out hexene or other comonomer (not shown) from the down-flowing solvent/diluent (not shown). The bottoms 26 from the separator 18, containing the catalyst, decene, and heavy solvent/diluent (if any), is predominately pumped back to the reactor 16. Heat exchangers (not shown) are in-line with the pump around flow. Where waxy buildup is an issue, spare heat exchangers may also be provided. For both the bubbling pot and the pumparound type reactor/separator configurations described above, a small portion of the bottoms stream 26, containing purge heavies, spent catalyst with heavy solvent/diluent (if any) 27, and decene is directed to an optional catalyst disposal and solvent/diluent recovery process 28. To minimize the load on solvent/diluent recovery process 28, it is desirable to have a catalyst with high productivity (grams of olefin converted divided by grams of catalyst used).

In the gas stream 22 from the gas/liquid phase separator 18, ethylene (also referred to as C2) is not recovered in high purity. This saves cryogenic ethylene column costs. Unconverted ethylene may be recycled back to the comonomer synthesis reactor 18, or sent on to another process (not shown), for example the downstream polyethylene polymerization process. Solvent/diluent and catalyst recycle 29 from the bottoms 26 of the gas/liquid phase separator 18 are sent back to the oligomerization reactor 16. Most octene products are swept out of the reactor or reactor/separator loop along with unconverted ethylene in the gas stream 22. The improved in-line reaction and separation process 10 does not include hexene/octene (also referred to as C6/C8) separation because some of the trace octene byproduct is used in the polymerization along with the hexene. Some trace octene may also exit the gas/liquid phase separator 18 in the bottoms stream 26 along with the decene (also referred to as C10) byproduct.

The improved reaction and separation process of the instant invention for generating monomer in a pre-reactor immediately before the polymerization reactor without isolation of the comonomer greatly simplifies the required process. The exemplary process schematic of FIG. 1 permits the number of separation towers to be reduced versus the standalone concept of producing comonomer. This results in significant operating and capital cost savings over conventional standalone processes for manufacturing comonomers, such as hexene. An additional benefit of the instant invention is that the continual removal of hexene from the comonomer synthesis reactor zone reduces the formation of decene byproduct. The improved reaction and separation process of the instant invention is compatible with a Phillips-type trimerization catalyst, but may also be useful with other homogeneous or heterogeneous selective oligomerization catalysts.

Figure 2:
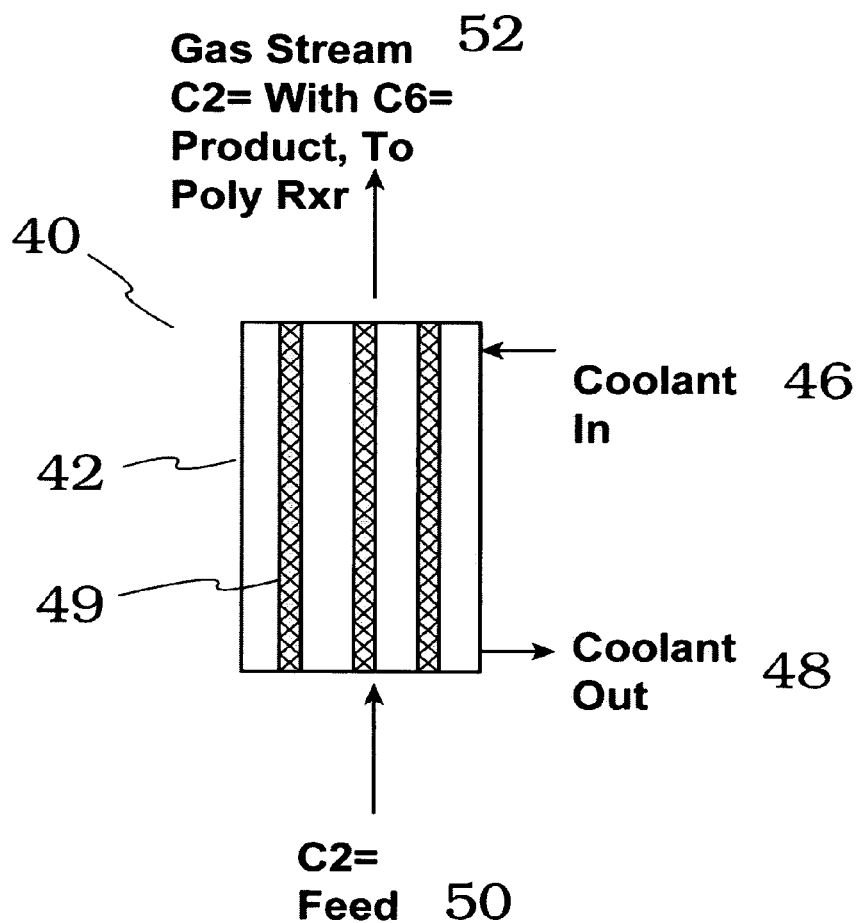
FIG. 2 depicts an illustrative schematic of the fixed bed reactors for in-line comonomer generation without a downstream gas/liquid phase separator in which catalyst is in the tubes with coolant.
Figure 3:
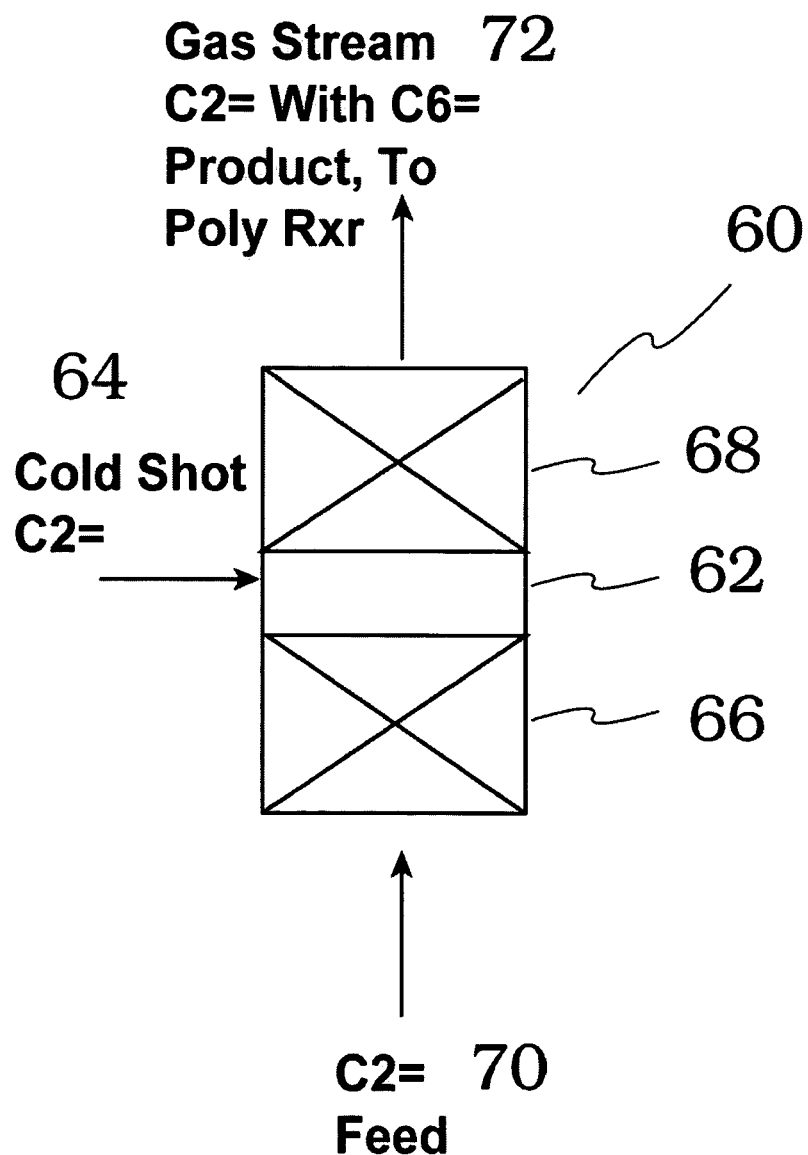
FIG. 3 depicts an illustrative schematic of the fixed bed reactors for in-line comonomer generation without a downstream gas/liquid phase separator in which cold shot cooling is utilized.
Figure 4:
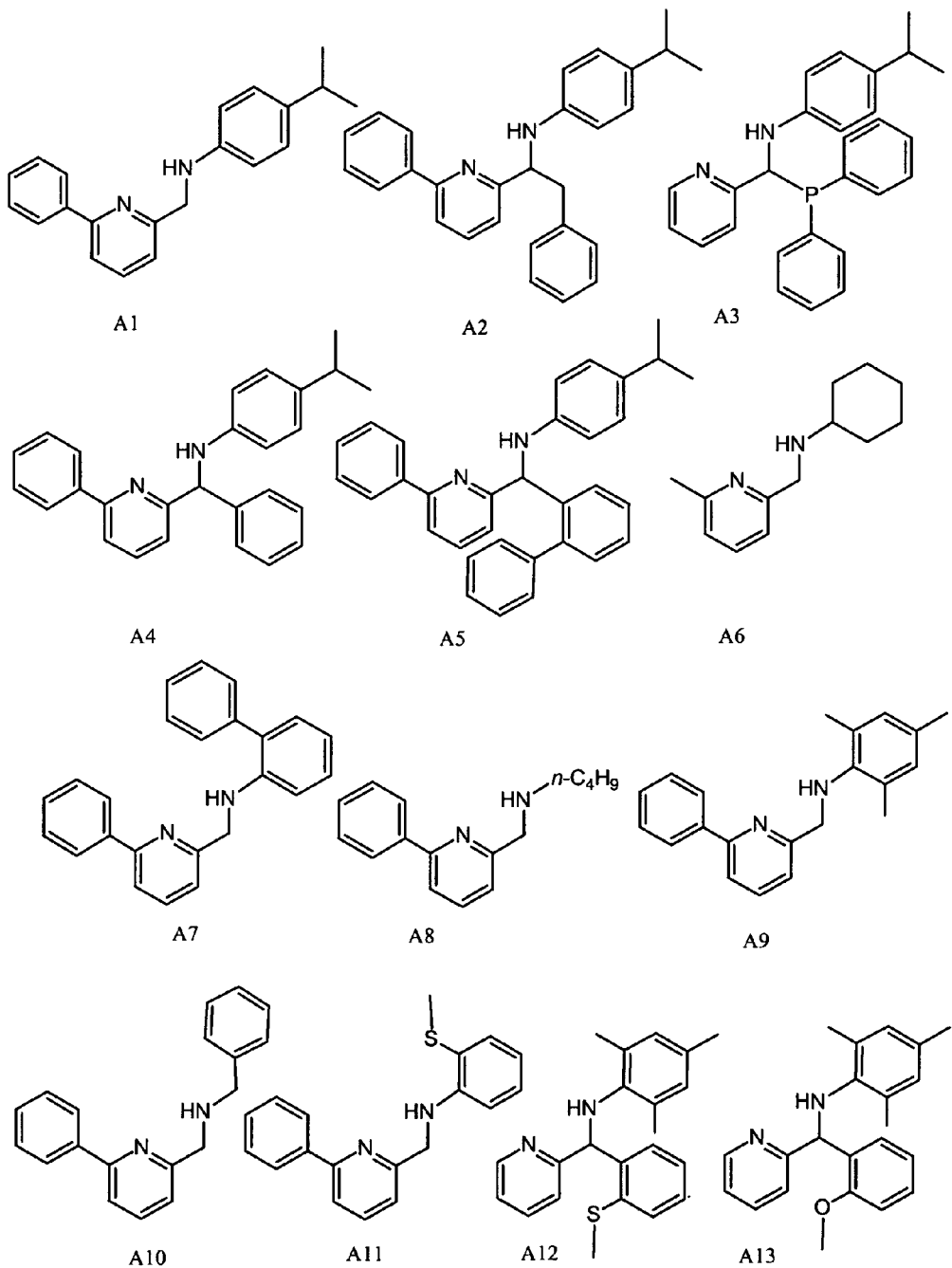
FIG. 4 illustrates pyridyl-amine ligands A1-A13.
Figure 5:
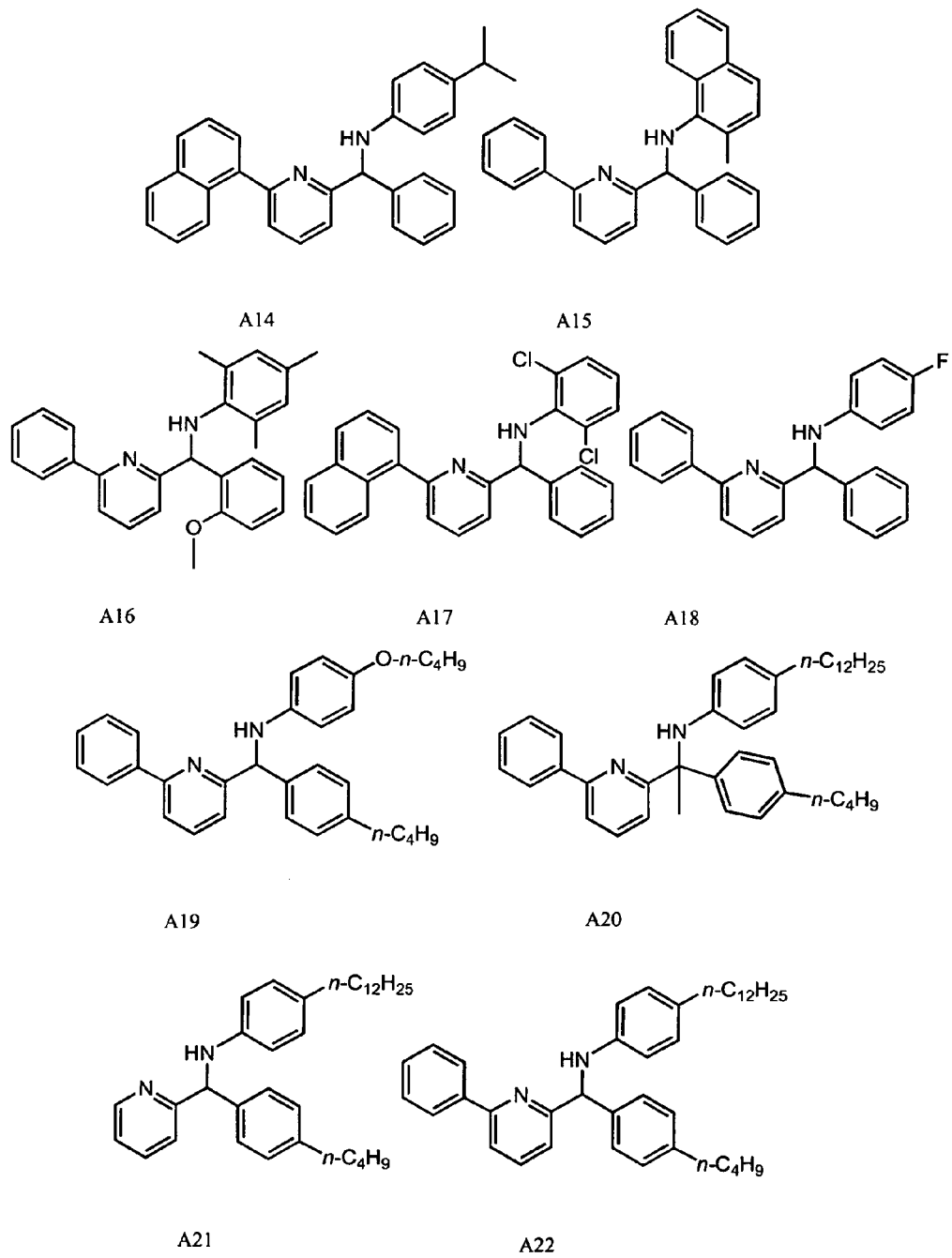
FIG. 5 illustrates pyridyl-amine ligands A14-A22.
Figure 6:
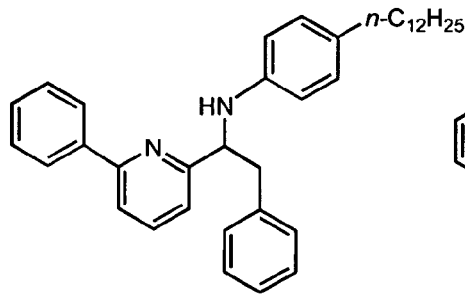
FIG. 6 illustrates pyridyl-amine ligands A23-A32.
Figure 6:
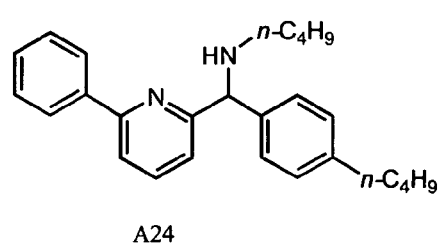
Figure 6:
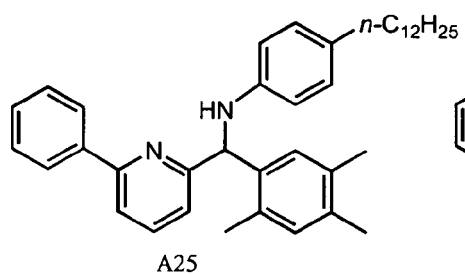
Figure 6:
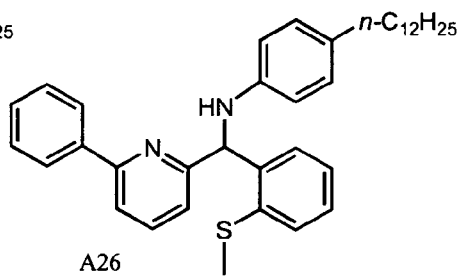
Figure 6:
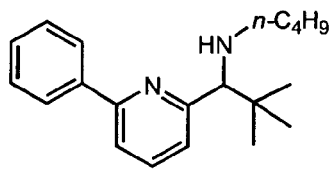
Figure 6:
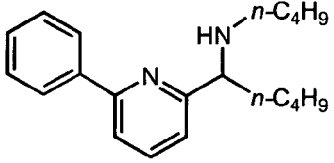
Figure 6:
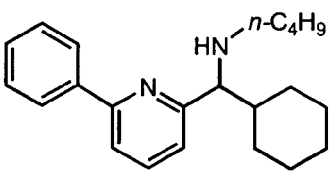
Figure 6:
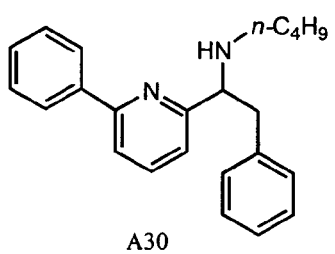
Figure 6:
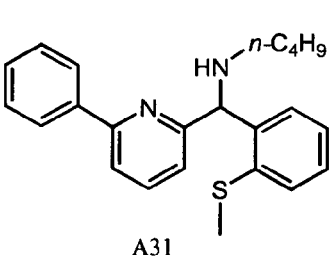
Figure 6:
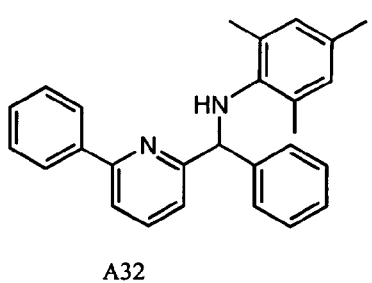
Figure 7:
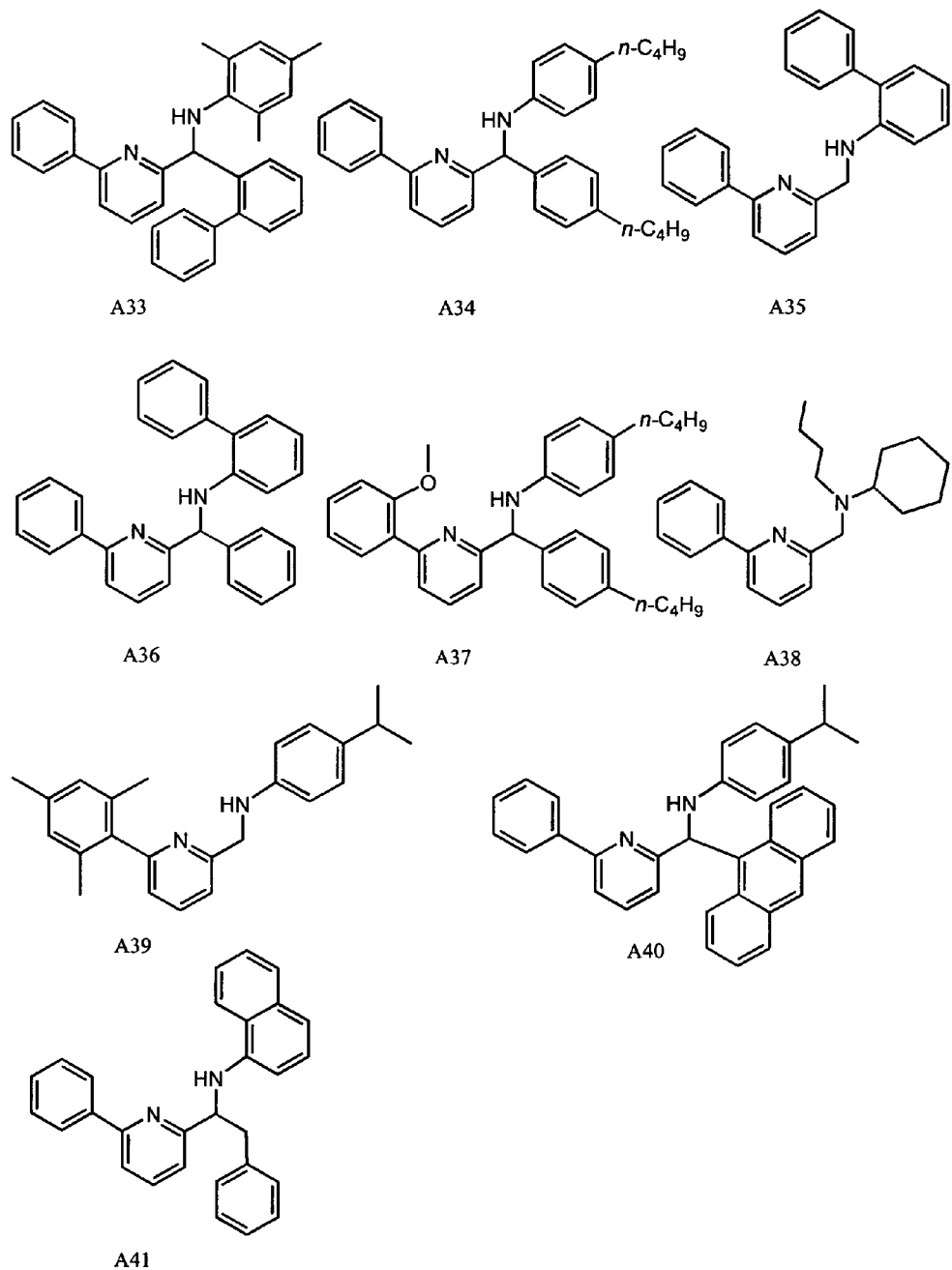
FIG. 7 illustrates pyridyl-amine ligands A33-A41.
Figure 8:
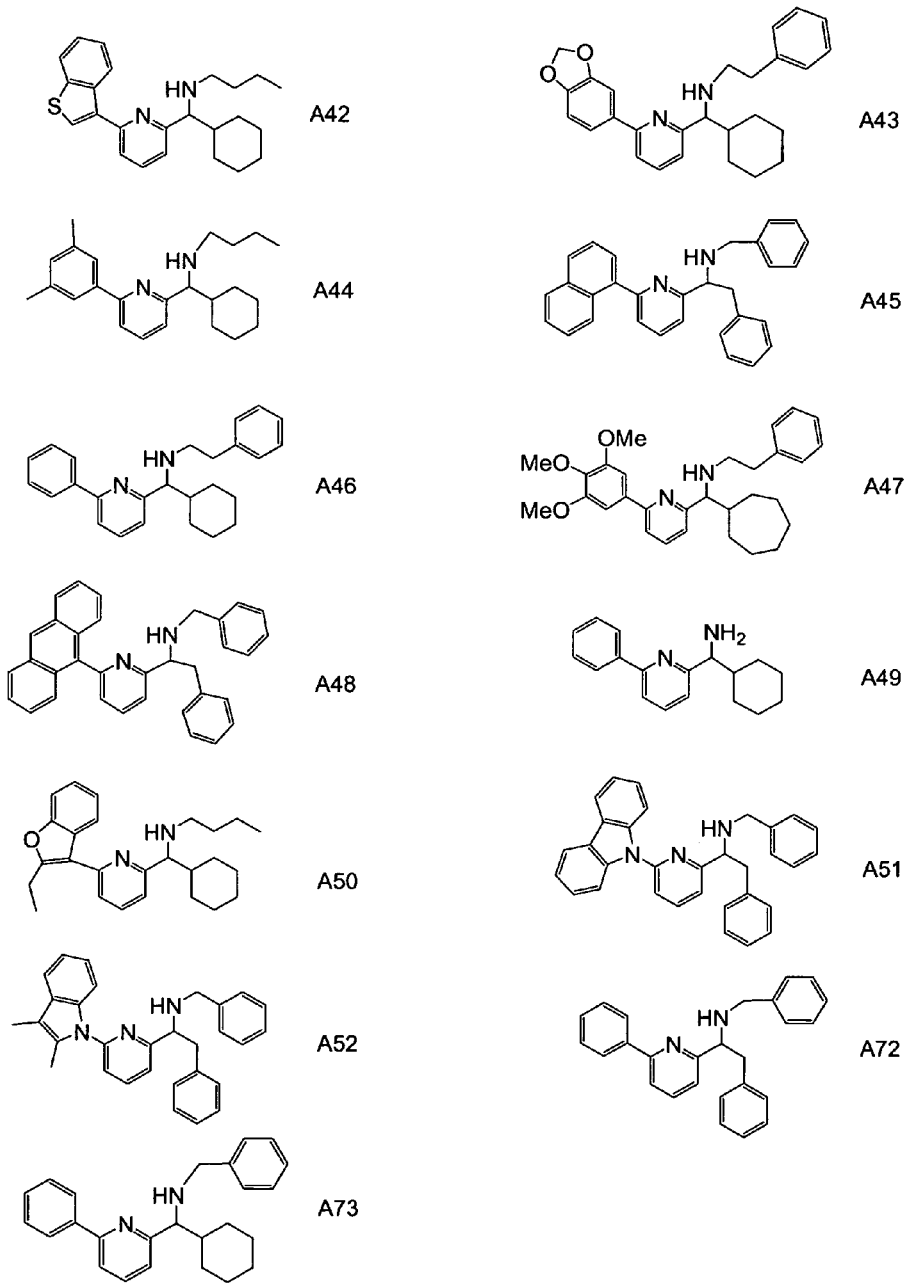
FIG. 8 illustrates pyridyl-amine ligands A42-A52.
Figure 9:
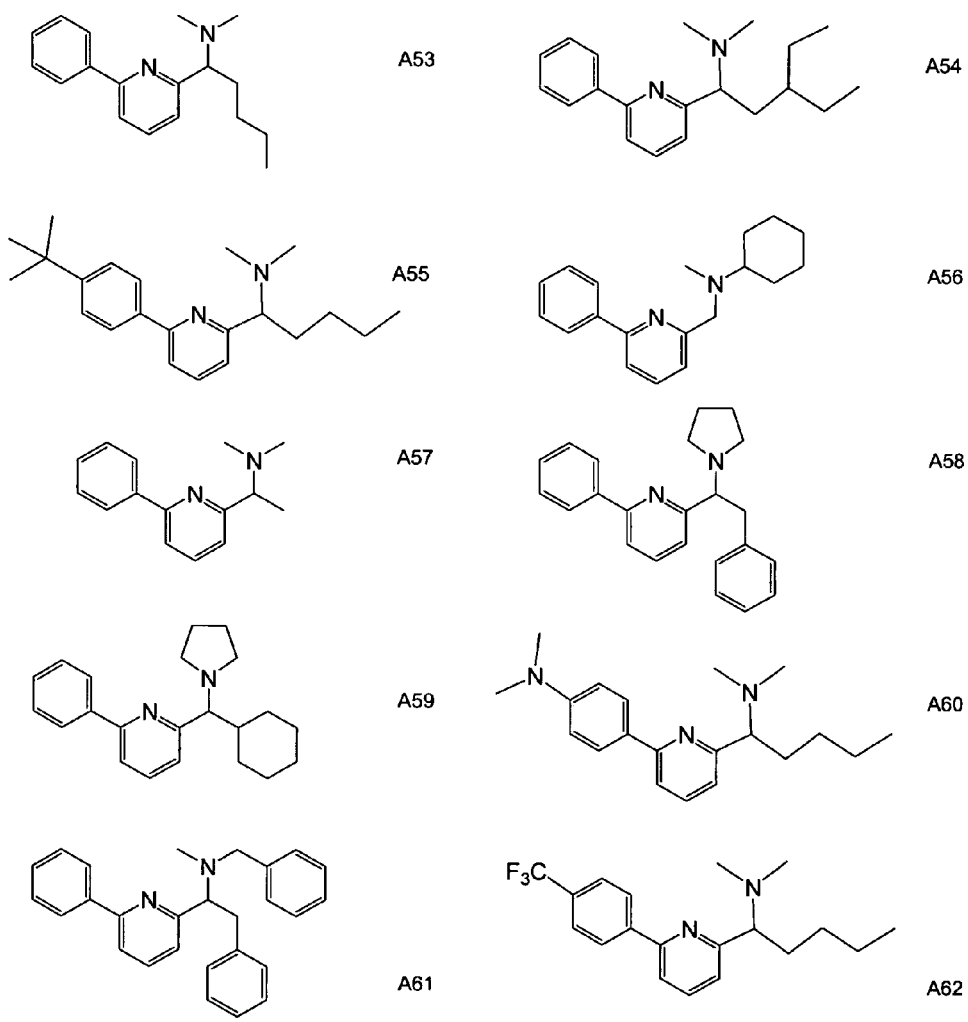
FIG. 9 illustrates pyridyl-amine ligands A53-A62
Figure 10:
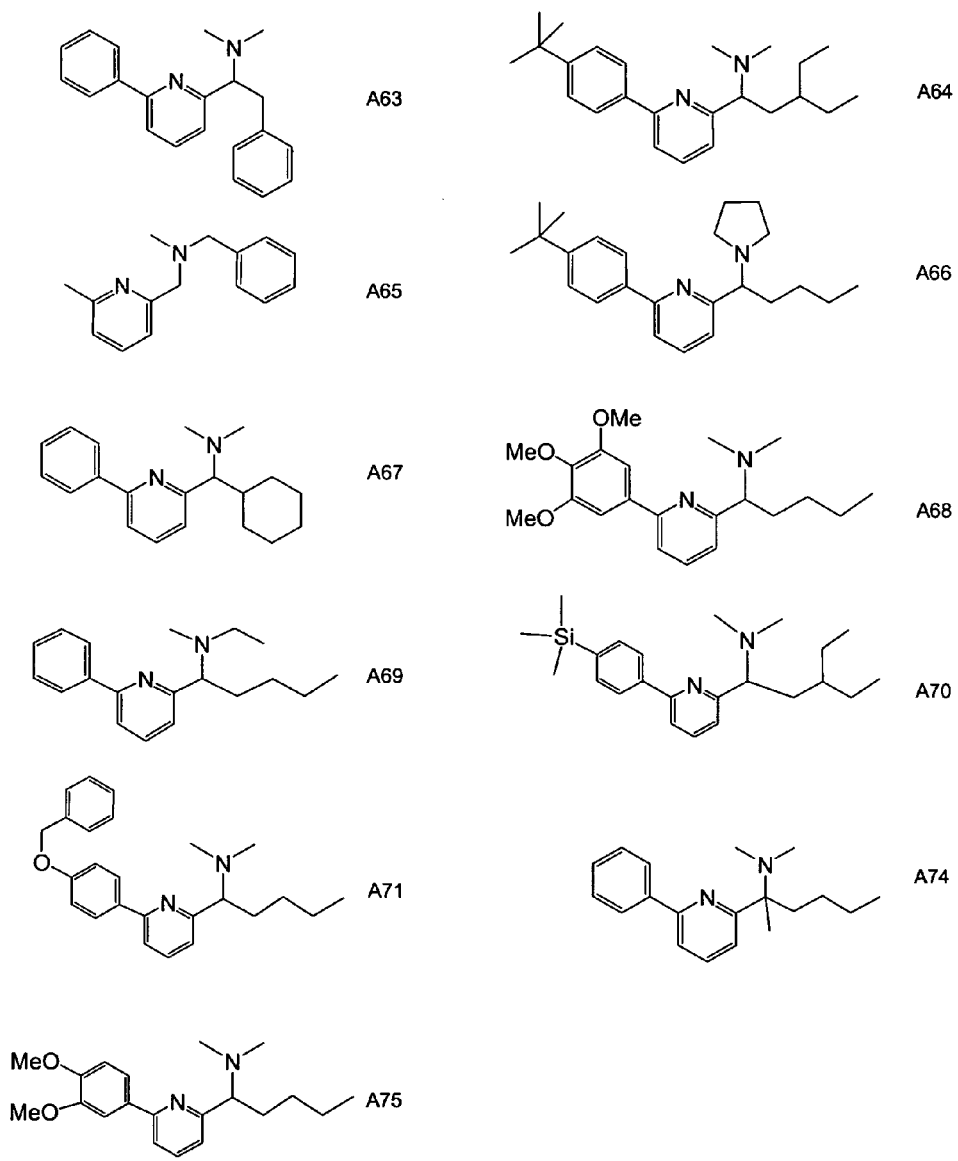
FIG. 10 illustrates pyridyl-amine ligands A63-A75.

FIGS. 2 and 3 depict two other exemplary process schematics of improved in-line comonomer generation processes 40, 60 of the instant invention that do not include a gas/liquid phase separator. These embodiments represent an even more simplified approach. In both FIGS. 2 and 3, fixed bed reactor types are used where the catalyst is in a fixed position, and ethylene is fed past it. Catalyst types may include, but are not limited to, chromium, vanadium, tantalum and titanium trimerization and/or tetramerization catalysts.

As comonomer (e.g. hexene) is produced, it is swept into the gas phase and carried out of the reactor. The precise form of the catalyst may include, but is not limited to, a solid, including active catalytic species anchored to a support, or in the form of a porous solid bed or monolith, which is wetted with soluble catalyst in a heavy solvent or diluent. The solvent/diluent with catalyst may be trickled through the bed, to renew the solvent/diluent over time.

In gas/solids systems, temperature control can be an issue. Using 47 kcal/mol hexene for heat of reaction, it can be estimated that for undiluted ethylene, a 10% conversion to hexene would generate about a 110 deg. C. temperature rise if there were no heat removal from the reactor. Also depicted in FIGS. 2 and 3 are two exemplary embodiments for managing the reaction heat generated.

In FIG. 2, the heat exchange capability is put into the reaction zone, for example, by loading the catalyst in 1"-6" diameter tubes surrounded by a cooling medium. FIG. 2 depicts a comonomer synthesis reactor 42 with catalyst in tubes 44 with coolant. Coolant enters and exits the comonomer synthesis reactor 42 through the coolant in 46 and coolant out 48 ports respectively. Ethylene (C2 feed) 50 enters the comonomer synthesis reactor 42 and reacts to form a gas stream 52 containing predominately ethylene (C2) along with comonomer, such as 1-hexene or 1-octene, which may be transferred directly to a downstream polyethylene polymerization reactor.

In FIG. 3, the reactor is divided into two or more catalyst beds, and cool feed or diluent is injected before each stage. FIG. 3 depicts a comonomer synthesis reactor 62 with cold shot cooling of C2 64 between the first reaction stage 66 and the second reaction stage 68 of the comonomer synthesis reactor 62. Ethylene (C2) feed 70 enters the comonomer synthesis reactor 62 and again reacts to form a gas stream 72 containing predominately ethylene (C2) along with comonomer, such as 1-hexene or 1-octene, which may be transferred directly to a downstream polyethylene polymerization reactor (not shown).

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law.

What is claimed is:

1. An in-line method for generating comonomer for input to a polyethylene polymerization reactor comprising the following steps:
   providing an in-line comonomer synthesis reactor and a downstream gas/liquid phase separator prior to a polyethylene polymerization reactor;
   feeding ethylene monomer and a catalyst in a solvent and/or diluent to said comonomer synthesis reactor;
   reacting said ethylene monomer and said catalyst in solvent and or diluent under reaction conditions to produce an effluent stream comprising ethylene monomer and comonomer selected from the group consisting of 1-hexene, 1-octene, 1-decene, and mixtures thereof;
   passing said effluent stream from said comonomer synthesis reactor to said downstream gas/liquid phase separator to continuously separate a gas stream from a bottoms stream, wherein said gas stream is a mixture of predominately ethylene monomer, 1-hexene and 1-octene and said bottoms stream is a mixture of catalyst, decene and solvent and/or diluent;
   purging from said bottom stream spent catalyst and purge heavies, and recycling said catalyst in solvent and/or diluent to said comonomer synthesis reactor; and
   passing said gas stream to said polyethylene polymerization reactor to provide a comonomer source, wherein the catalyst comprises the combination of:

1) a ligand represented by the formula:

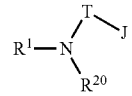

wherein:
   N is nitrogen;
   $R^1$ and $R^{20}$ are each independently selected from the group consisting of hydrogen and optionally substituted hydrocarbyl, heteroatom containing hydrocarbyl and silyl, provided that $R^1$ or $R^{20}$ do not equal T-J, alternately $R^1$ and $R^{20}$ are each independently a ring having from 4 to 8 atoms in the ring selected from the group consisting of substituted cycloalkyl, heterocycloalkyl, aryl and heteroaryl);
   T is a bridging group, represented by the formula -(T'$R^2R^3$)—, where T' is carbon or silicon, $R^2$ and $R^3$ are each independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, provided that two or more $R^2$ and/or $R^3$ groups may be joined together to form one or more optionally substituted ring systems having from 3 to 50 non-hydrogen atoms;
   J is an optionally substituted six-membered heterocycle, containing at least one nitrogen atom as part of the ring, or J is an optionally substituted five-membered heterocycle, containing at least one nitrogen atom as part of the ring;

2) a metal precursor compound characterized by the general formula Cr(L)$_n$ where each L is independently selected from the group consisting of halide, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, wherein two or more L groups may be combined in a ring structure having from 3 to 50 non-hydrogen atoms; and n is 1, 2, 3, 4, 5, or 6; and 3) optionally, one or more activators.

2. The in-line method of claim 1, wherein said gas stream is not stored or isolated prior to entering said polyethylene polymerization reactor.

3. The in-line method of claim 1, wherein said comonomer synthesis reactor is a stirred tank reactor, more than one agitated vessel in series, or a tube-like contactor.

4. The in-line method of claim 1, wherein the ligand is represented by the formula:

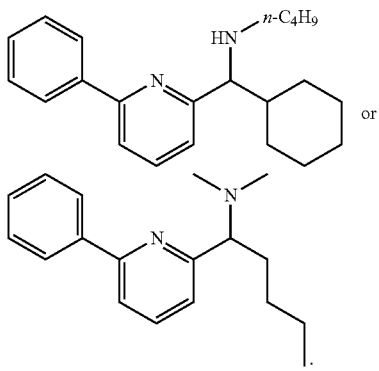

5. The in-line method of claim 1, wherein said catalyst comprises one or more activators.

6. The in-line method of claim 1, wherein said solvent and or diluents has a volatility less than 1-hexene and 1-octene.

7. The in-line method of claim 1, wherein said solvent and or diluent is selected from the group consisting of isobutane, isopentane, cycloparaffins, and aromatics.

8. The in-line method of claim 1, wherein said reaction conditions yield from about 5% to about 75% conversion of said ethylene monomer.

9. The in-line method of claim 7, wherein said reaction conditions yield from about 10% to about 50% conversion of said ethylene monomer.

10. The in-line method of claim 8, wherein said reaction conditions comprise a reaction temperature from about 80 to about 150° C., a reaction pressure from about 300 to about 700 psi, and a reaction residence time from about 30 minutes to about 4 hours.

11. The in-line method of claim 1, wherein a catalyst deactivator is added to said effluent stream exiting from said comonomer synthesis reactor.

12. The in-line method of claim 11, wherein said catalyst deactivator is water or alcohol.

13. The in-line method of claim 1, wherein said gas/liquid phase separator comprises a knockout vessel, a stirred tank or pot, or other one-stage phase separator.

14. The in-line method of claim 13, wherein said gas/liquid phase separator further comprises trays or packing in the vapor zone.

15. The in-line method of claim 1, wherein said bottoms stream comprises ethylene monomer, spent catalyst, purge heavies, catalyst in solvent and or diluent, 1-octene and 1-decene.

16. The in-line method of claim 1 further comprising the step of adding ethylene monomer to said gas/liquid phase separator to strip out comonomer from down-flowing solvent and or diluent.

17. The in-line method of claim 1 further comprising the step of directing to a catalyst disposal and solvent and or diluent recovery process said purge stream of spent catalyst and purge heavies.

18. An in-line method for generating comonomer for input to a polyethylene polymerization reactor comprising the following steps:
providing an in-line comonomer synthesis reactor having two or more reaction stages prior to a polyethylene polymerization reactor, wherein the reactor is a fixed bed type with a catalyst in a fixed position;
feeding ethylene monomer to said comonomer synthesis reactor;
reacting said ethylene monomer and said catalyst under reaction conditions to produce an effluent stream comprising ethylene monomer and comonomer selected from the group consisting of 1-hexene, 1-octene; 1-decene and mixtures thereof;
continuously separating said effluent stream from said comonomer synthesis reactor into a gas stream which is a mixture of predominately ethylene monomer, 1-hexene and 1-octene and a bottoms stream which is a mixture of catalyst, decene and solvent and/or diluent; and
directing said gas stream to said polyethylene polymerization reactor to provide a comonomer source, wherein the catalyst comprises the combination of:

1) a ligand represented by the formula:

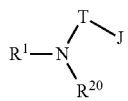

wherein:

N is nitrogen;

$R^1$ and $R^{20}$ are each independently selected from the group consisting of hydrogen and optionally substituted hydrocarbyl, heteroatom containing hydrocarbyl and silyl, provided that $R^1$ or $R^{20}$ do not equal T-J, alternately $R^1$ and $R^{20}$ are each independently a ring having from 4 to 8 atoms in the ring selected from the group consisting of substituted cycloalkyl, heterocycloalkyl, aryl and heteroaryl);

T is a bridging group, represented by the formula -(T'$R^2R^3$)—, where T' is carbon or silicon, $R^2$ and $R^3$ are each independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, provided that two or more $R^2$ and/or $R^3$ groups may be joined together to form one or more optionally substituted ring systems having from 3 to 50 non-hydrogen atoms;

J is an optionally substituted six-membered heterocycle, containing at least one nitrogen atom as part of the ring, or J is an optionally substituted five-membered heterocycle, containing at least one nitrogen atom as part of the ring;

2) a metal precursor compound characterized by the general formula $Cr(L)_n$ where each L is independently selected from the group consisting of halide, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, wherein two or more L groups may be combined in a ring structure having from 3 to 50 non-hydrogen atoms; and n is 1, 2, 3, 4, 5, or 6; and 3) optionally, one or more activators.

19. The in-line method of claim 18, wherein said gas stream is not stored or isolated prior to entering said polyethylene polymerization reactor.

20. The in-line method of claim 18, wherein said catalyst in a fixed position is in the form of an active catalytic species anchored to a support, a porous bed, or a monolith.

21. The in-line method of claim 20, wherein the ligand of said catalyst in a fixed position is selected from the group consisting of

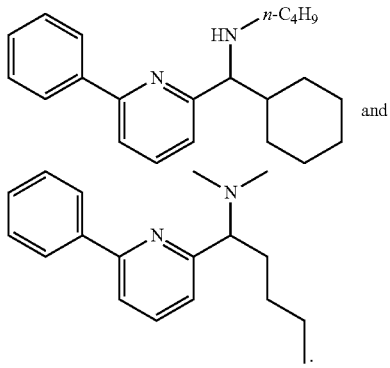

22. The in-line method of claim 21, wherein said catalyst in a fixed position comprises activator.

23. The in-line method of claim 18 further comprising the step of trickling solvent and or diluent with catalyst through said comonomer synthesis reactor to renew said catalyst in a fixed position.

24. The in-line method of claim 18, wherein said comonomer synthesis reactor is cooled by circulating a cooling medium around tubes loaded with said catalyst in a fixed position.

25. The in-line method of claim 18, wherein said comonomer synthesis reactor is cooled by injecting cold ethylene monomer between reaction stages.

26. The in-line method of claim 18, wherein said reaction conditions yield from about 5% to about 75% conversion of said ethylene monomer.

27. The in-line method of claim 26, wherein said reaction conditions yield from about 10% to about 50% conversion of said ethylene monomer.

28. The in-line method of claim 26, wherein said reaction conditions comprise a reaction temperature from about 80 to about 150° C., a reaction pressure from about 300 to about 700 psi, and a reaction residence time from about 30 minutes to about 4 hours.

29. The in-line method of claim 18, wherein a catalyst deactivator is added to said effluent stream exiting from said comonomer synthesis reactor.

30. The in-line method of claim 29, wherein said catalyst deactivator is water or alcohol.

31. An in-line method for generating comonomer for input to a polyethylene polymerization reactor comprising the following steps:
providing an in-line comonomer synthesis reactor and a downstream gas/liquid phase separator prior to a polyethylene polymerization reactor;
feeding ethylene monomer and a catalyst in a solvent and or diluent to said comonomer synthesis reactor;
reacting said ethylene monomer and said catalyst in solvent and or diluent under reaction conditions to produce an effluent stream comprising ethylene monomer and comonomer selected from the group consisting of 1-hexene, 1-octene; 1-decene and mixtures thereof;
passing said effluent stream from said comonomer synthesis reactor to said downstream gas/liquid phase separator to continuously separate a gas stream from a bottom stream, wherein said gas stream is a mixture of predominately ethylene monomer, 1-hexene and 1-octene and said bottoms stream is a mixture of catalyst, decene and solvent and/or diluent; and
transporting without isolation or storage said gas stream to said polyethylene polymerization reactor to provide a comonomer source, wherein the catalyst comprises the combination of:

1) a ligand represented by the formula:

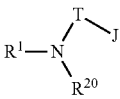

wherein:
N is nitrogen;
$R^1$ and $R^{20}$ are each independently selected from the group consisting of hydrogen and optionally substituted hydrocarbyl, heteroatom containing hydrocarbyl and silyl, provided that $R^1$ or $R^{20}$ do not equal T-J, alternately $R^1$ and $R^{20}$ are each independently a ring having from 4 to 8 atoms in the ring selected from the group consisting of substituted cycloalkyl, heterocycloalkyl, aryl and heteroaryl);
T is a bridging group, represented by the formula -(T'$R^2R^3$)—, where T' is carbon or silicon, $R^2$ and $R^3$ are each independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, provided that two or more $R^2$ and/or $R^3$ groups may be joined together to form one or more optionally substituted ring systems having from 3 to 50 non-hydrogen atoms;
J is an optionally substituted six-membered heterocycle, containing at least one nitrogen atom as part of the ring, or J is an optionally substituted five-membered heterocycle, containing at least one nitrogen atom as part of the ring;
2) a metal precursor compound characterized by the general formula $Cr(L)_n$ where each L is independently selected from the group consisting of halide, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, wherein two or more L groups may be combined in a ring structure having from 3 to 50 non-hydrogen atoms; and n is 1, 2, 3, 4, 5, or 6; and
3) optionally, one or more activators.

32. The in-line method of claim 31, wherein the ligand in said catalyst is selected from the group consisting of:

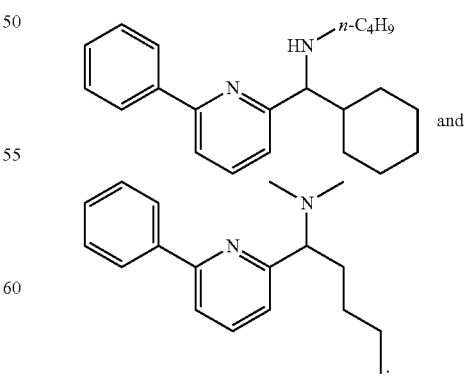

* * * * *